US009592295B2

(12) United States Patent
Lu et al.

(10) Patent No.: US 9,592,295 B2
(45) Date of Patent: *Mar. 14, 2017

(54) REVERSELY THERMO-REVERSIBLE HYDROGEL COMPOSITIONS

(71) Applicant: Broda Technologies Co., Ltd., Shanghai (CN)

(72) Inventors: Shao Xiang Lu, Plainsboro, NJ (US); Jeffrey Lu, Plainsboro, NJ (US); Letian Liu, Plainsboro, NJ (US)

(73) Assignee: Broda Technologies Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,427

(22) Filed: Feb. 26, 2016

(65) Prior Publication Data

US 2016/0175445 A1 Jun. 23, 2016

Related U.S. Application Data

(60) Continuation of application No. 14/492,288, filed on Sep. 22, 2014, now abandoned, which is a division of
(Continued)

(51) Int. Cl.
| | |
|---|---|
| *A61K 47/10* | (2006.01) |
| *A61K 31/565* | (2006.01) |
| *A61K 31/60* | (2006.01) |
| *A61K 31/573* | (2006.01) |
| *A61K 31/416* | (2006.01) |
| *A61Q 19/08* | (2006.01) |
| *A61K 8/368* | (2006.01) |
| *A61Q 1/02* | (2006.01) |
| *A61K 8/90* | (2006.01) |
| *A01N 37/18* | (2006.01) |
| *A61K 8/37* | (2006.01) |
| *A61Q 17/04* | (2006.01) |
| *A61Q 1/00* | (2006.01) |
| *A61Q 1/04* | (2006.01) |

(Continued)

(52) U.S. Cl.
CPC .............. *A61K 47/10* (2013.01); *A01N 25/00* (2013.01); *A01N 37/18* (2013.01); *A61K 8/02* (2013.01); *A61K 8/042* (2013.01); *A61K 8/345* (2013.01); *A61K 8/368* (2013.01); *A61K 8/37* (2013.01); *A61K 8/39* (2013.01); *A61K 8/86* (2013.01); *A61K 8/90* (2013.01); *A61K 8/97* (2013.01); *A61K 9/0014* (2013.01); *A61K 9/06* (2013.01); *A61K 31/137* (2013.01); *A61K 31/167* (2013.01); *A61K 31/416* (2013.01); *A61K 31/506* (2013.01); *A61K 31/565* (2013.01); *A61K 31/573* (2013.01); *A61K 31/58* (2013.01); *A61K 31/60* (2013.01); *A61K 47/14* (2013.01); *A61K 47/34* (2013.01); *A61K 47/48215* (2013.01); *A61Q 1/00* (2013.01); *A61Q 1/02* (2013.01); *A61Q 1/04* (2013.01); *A61Q 1/12* (2013.01); *A61Q 5/00* (2013.01); *A61Q 5/10* (2013.01); *A61Q 7/00* (2013.01); *A61Q 9/02* (2013.01); *A61Q 9/04* (2013.01); *A61Q 11/00* (2013.01); *A61Q 13/00* (2013.01); *A61Q 15/00* (2013.01); *A61Q 17/02* (2013.01); *A61Q 17/04* (2013.01); *A61Q 19/00* (2013.01); *A61Q 19/08* (2013.01); *C08J 3/075* (2013.01); *C08L 71/02* (2013.01); *A61K 2800/54* (2013.01); *A61K 2800/548* (2013.01); *C08G 2210/00* (2013.01); *C08G 2650/58* (2013.01); *C08L 2203/02* (2013.01)

(58) Field of Classification Search
None
See application file for complete search history.

(56) References Cited

U.S. PATENT DOCUMENTS

| | | |
|---|---|---|
| 4,188,373 A | 2/1980 | Krezanoski |
| 4,474,751 A | 10/1984 | Haslam et al. |

(Continued)

FOREIGN PATENT DOCUMENTS

| | | |
|---|---|---|
| CN | 1753949 A | 3/2006 |
| CN | 1869128 A | 11/2006 |

(Continued)

OTHER PUBLICATIONS

Office Action in U.S. Appl. No. 14/548,851 mailed Mar. 30, 2016.
"Introduction and Concepts," 09_Nano09, downloaded from cqm.um.pt.
"Materials Safety Data Sheet, SupraSalix-16," Brodatech, Material Safety Data Sheet, Sep. 23, 2014, 2 pages.
"SupaSalix-16," Brodatech, Product Specifications, Sep. 30, 2014, 1 page.
"SupraSalix-16," Brodatech, Technical Data Sheet, 1 page.
2006 BASF Technical Bulletin entitled "Pluronic® F127 surfactant viscosity as a function of temperature & concentration".
BASF The Chemical Company, "Lutrol® L and Lutrol® F-Grades", Apr. 2010, pp. 1-8.

(Continued)

*Primary Examiner* — Jianfeng Song
(74) *Attorney, Agent, or Firm* — RatnerPrestia

(57) ABSTRACT

A reversely thermo-reversible hydrogel composition comprising a water soluble block copolymer comprising at least two blocks of polyethylene oxide and at least one block of polypropylene oxide, and at least one associative gelling adjuvant having water solubility less than 0.5 g/100 ml, preferably less than 0.3 g/100 ml at 20° C., and being capable of forming water soluble inter-molecular complexes with the water soluble block copolymer in water. The hydrogel composition exhibits improved gelling efficiency, enhanced solubility and/or stability for water sparely soluble and insoluble pharmaceutical agents. The hydrogel compositions are useful in a variety of pharmaceutical and cosmetic products and applications, such as esophageal, otic, vaginal, rectal, ophthalmic, treatments of disorders and imperfections of the skin, and treating and/or preventing alopecia and restoring and/or promoting hair growth.

20 Claims, No Drawings

Related U.S. Application Data application No. 13/425,923, filed on Mar. 21, 2012, now Pat. No. 8,865,143, which is a continuation of application No. PCT/CN2011/000462, filed on Mar. 21, 2011.

(51) Int. Cl.

| | | |
|---|---|---|
| *A61Q 5/00* | (2006.01) | |
| *A61Q 5/10* | (2006.01) | |
| *A61Q 9/02* | (2006.01) | |
| *A61Q 9/04* | (2006.01) | |
| *A61Q 11/00* | (2006.01) | |
| *A61Q 13/00* | (2006.01) | |
| *A61Q 15/00* | (2006.01) | |
| *A61Q 17/02* | (2006.01) | |
| *A61Q 19/00* | (2006.01) | |
| *A61K 8/97* | (2006.01) | |
| *A61K 47/34* | (2006.01) | |
| *A61K 8/02* | (2006.01) | |
| *A61K 31/137* | (2006.01) | |
| *A61K 31/167* | (2006.01) | |
| *A61K 31/506* | (2006.01) | |
| *A61K 31/58* | (2006.01) | |
| *A01N 25/00* | (2006.01) | |
| *A61K 9/00* | (2006.01) | |
| *A61K 9/06* | (2006.01) | |
| *A61K 8/39* | (2006.01) | |
| *A61Q 7/00* | (2006.01) | |
| *A61K 8/86* | (2006.01) | |
| *A61K 8/04* | (2006.01) | |
| *C08J 3/075* | (2006.01) | |
| *A61K 8/34* | (2006.01) | |
| *A61K 47/48* | (2006.01) | |
| *A61Q 1/12* | (2006.01) | |
| *C08L 71/02* | (2006.01) | |
| *A61K 47/14* | (2006.01) | |

(56) References Cited

U.S. PATENT DOCUMENTS

| | | | |
|---|---|---|---|
| 4,478,822 A | 10/1984 | Haslam et al. | |
| 4,810,503 A | 3/1989 | Carson | |
| 5,187,191 A | 2/1993 | Otten et al. | |
| 5,208,031 A | 5/1993 | Kelly | |
| 5,252,318 A | 10/1993 | Joshi et al. | |
| 5,256,396 A | 10/1993 | Piechota, Jr. | |
| 5,266,321 A | 11/1993 | Shukuzaki et al. | |
| 5,298,260 A | 3/1994 | Viegas | |
| 5,538,793 A | 7/1996 | Inokuchi et al. | |
| 5,593,683 A | 1/1997 | Viegas et al. | |
| 5,629,260 A | 5/1997 | Utz et al. | |
| 6,316,011 B1 | 11/2001 | Ron et al. | |
| 6,713,093 B2 | 3/2004 | Takahata et al. | |
| 8,865,143 B2 | 10/2014 | Lu et al. | |
| 2004/0158941 A1 | 8/2004 | Geary et al. | |
| 2005/0220831 A1* | 10/2005 | Jorsal | A61K 8/068 424/401 |
| 2007/0211212 A1* | 9/2007 | Bennwik | A61B 3/0008 351/221 |
| 2009/0196942 A1* | 8/2009 | Goyarts | A61K 8/97 424/736 |
| 2009/0325938 A1 | 12/2009 | Lichter et al. | |
| 2010/0105801 A1 | 4/2010 | Choi | |
| 2010/0150850 A1 | 6/2010 | Tamor | |
| 2012/0244097 A1 | 9/2012 | Lu et al. | |

FOREIGN PATENT DOCUMENTS

| | | |
|---|---|---|
| CN | 101536974 A | 9/2009 |
| GB | 1 207 438 | 9/1970 |
| JP | 04225914 | 8/1992 |
| JP | 11222419 | 8/1999 |
| JP | 2006519272 | 8/2006 |
| JP | 2010-520943 | 6/2010 |
| WO | 2004076561 | 9/2004 |
| WO | WO 2004/076561 A1 | 9/2004 |
| WO | WO 2010/006376 A1 | 1/2010 |

OTHER PUBLICATIONS

Entire patent prosecution history of U.S. Appl. No. 13/425,923, filed Mar. 21, 2012, entitled "Reversely Thermo-Reversible Hydrogel Compositions," now U.S. Pat. No. 8,865,143, issued Oct. 21, 2014.
Entire patent prosecution history of U.S. Appl. No. 14/492,288, filed Sep. 22, 2014, entitled "Reversely Thermo-Reversible Hydrogel Compositions".
Entire patent prosecution history of U.S. Appl. No. 14/548,851, filed Nov. 20, 2014, entitled "Water-Soluble Supramolecular Complexes".
Extended European Search Report mailed Jul. 16, 2014 in counterpart European Application No. 11861767.9-1460.
Lehn, *Angew. Chem. Int. Ed. Engl.*, vol. 29, pp. 1304-1319 (1990).
The HLB System A Time-Saving Guide to Emulsifier Selection, © 1976 ICI Americas Inc., pp. 1-22.
The HLB System A Time-Saving Guide to Surfactant Selection, Uniqema Presentation, Mar. 9, 2004, 39 pages.
European Office Action for European Application No. 13120.001-00155, dated Apr. 12, 2016, 5 pages.
Decision to Grant dated Jul. 19, 2016 for Japanese Application No. 2014-500219, including English translation, 6 pages.
Final Office Action dated Jul. 14, 2016 for U.S. Appl. No. 14/548,851, 12 pages.

* cited by examiner

REVERSELY THERMO-REVERSIBLE HYDROGEL COMPOSITIONS

CROSS-REFERENCE TO RELATED APPLICATIONS

This application is a continuation of U.S. application Ser. No. 14/492,288 filed on Sep. 22, 2014, which is a divisional of U.S. application Ser. No. 13/425,923, filed Mar. 21, 2012 which is a continuation of International Application No. PCT/CN2011/000462, filed Mar. 21, 2011, the contents of which are incorporated by reference herein in their entireties and for all purposes.

BACKGROUND

The field of applying active ingredients topically to humans and animals is, of course, wide ranging and comprises for example, the application of active ingredients for pharmaceutical and cosmetic purposes. It is specifically desirable to provide such compositions in a reversely thermo-reversible hydrogel form, which remains in contact with the applied target and has controlled or sustained release of active ingredients over an extended period of time. The gel form of reversely thermo-reversible hydrogel compositions would seem to offer the best potential in terms of ease of manufacture for filling, preventing the possible re-crystallization or settling of active ingredients during storage, easy and uniform spreading during application, prolonged residence time, and controlled or sustained release of active ingredients.

Reversely thermo-reversible gelling systems are known in which the solution viscosity increases and decreases with an increase and decrease in temperature, respectively. Such system exhibits a solution to gel (sol-gel) transition which transforms a low viscosity solution to a higher viscosity gel form as the temperature increases, with continued increases in temperature, the gelled system then experiences a gel to solution (gel-sol) transition which transforms the gelled system back to a liquid solution. Such reversely thermo-reversible gelling systems are useful wherever it is desirable to handle a composition in a liquid state, and/or the performance of the composition in a gel form.

A known material with these properties is a reversely thermo-reversible hydrogel using water soluble block copolymers of polyethylene oxide and polypropylene oxide available commercially as Pluronic® from BASF (Ludwigshafen, Germany) and generically known as Poloxamers. Generally, about 20% w/w Pluronic® F127 aqueous solution is liquid when at below about 25° C. or heated to temperatures exceeding 70° C., but turns into gel form and exhibits maximum viscosity in the range of 30-60° C. (see 2006 BASF Technical Bulletin entitled "Pluronic® F127 surfactant viscosity as a function of temperature & concentration"; and April 2010 "Lutrol® L and Lutrol® F-Grades"). Typically, concentrations of Pluronic® F127 polymer of at least 18-20% by weight are needed to produce a sol-gel transition temperature at about 25° C. room temperature range. To decrease the desired sol-gel transition temperature further below 25° C., a higher concentration of Poloxamer polymer has to be used which in turn increases the viscosity of solution and results in unfavorable physiological interaction during use. The freedom to use Poloxamer polymers with adjustable sol-gel transition temperatures, specifically, at temperatures below about 25° C. without employing higher concentrations of polymer, is limited.

U.S. Pat. Nos. 4,188,373, 4,478,822 and 4,474,751 disclose the use of non-ionic block copolymers of polyethylene oxide and polypropylene oxide Poloxamers in aqueous pharmaceutical compositions. In these systems, the concentration of polymer is adjusted to give the desired sol-gel transition temperature. However, concentrations of the poloxamer polymer of at least 18-20% by weight are needed to produce a composition which exhibits such a transition at commercially or physiologically useful temperatures. Also, solutions containing more than 18-20% by weight of block copolymer at the desired sol-gel transition temperature are typically very viscous even in the "liquid" state. In addition, the high polymer concentrations may cause the material itself unfavorable physiological interactions with target tissue during use.

U.S. Pat. No. 5,256,396 to Piechota et al. discloses an oral composition of a water dispersible active ingredient with the use of Pluronic F127. These compositions are flowable liquids below 82° F. (27.8° C.), and gels when heated to 82° F. (27.8° C.).

U.S. Pat. No. 5,252,318 to Joshi et al discloses reversible gelling compositions which comprise of a blend of a pH-sensitive gelling polymer and a thermo-sensitive gelling polymer, such as Pluronic F 127. The sol-gel transition temperature adjustment has been achieved at relatively low Pluronic F127 polymer concentration upon simultaneous change in temperature and pH.

U.S. Pat. No. 6,316,011 to Ron et al discloses a reversely thermo-sensitive gelling composition comprising an end-modified block copolymer of polyethylene oxide and polypropylene oxide, the composition reversibly gelling at a temperature in the range of 22° C. to 40° C.

The prior art is mostly focused on the reversely thermo-reversible hydrogel compositions which are in a liquid state at room temperature or below, subsequently transform to a gel form when warmed to body temperature after application, and have to employ a high concentration of polymer. However, for many pharmaceutical and cosmetic products and applications, a gel form hydrogel composition is more preferred under use conditions. In addition, the liquid state of such systems at room temperature presents a lot of challenges in regard to the solubility and/or stability of sparely soluble or insoluble active ingredients in such aqueous liquid solutions. For example, the use of Salicylic acid or its derivatives for treating dandruff, acne, skin wrinkling, skin pigmentation, warts, freckles, or skin-related problems is well known in the preparation of dermatologic and cosmetic formulations. Salicylic acid or its derivatives are usually in crystalline form and are not sufficiently soluble in water or oils traditionally used in dermatological and cosmetic preparations. Typical problems which occur when using Salicylic acid or its derivatives in making dermatologic and cosmetic products are that the Salicylic acid or its derivatives tend to crystallize out within various compositions, which significantly reduces the bioavailability of Salicylic acid or its derivatives for treating or preventing the aforementioned skin problems. Further, Salicylic acid or its derivatives provide formulations that form crystals on standing and precipitate out within the solution, which are unpleasant with regard to texture and appearance from the consumer's viewpoint.

Accordingly, there remains a need for improved hydrogel compositions containing water soluble block copolymers of polyethylene oxide and polypropylene oxide, particularly reversely thermo-reversible hydrogel compositions containing such block copolymers of polyethylene oxide and polypropylene oxide, which have extended gel form under use conditions, specifically at below room temperature, and have acceptable or improved solubility and/or stability for sparsely soluble or insoluble active ingredients at relatively low polymer concentration, useful for pharmaceutical and cosmetic products and applications, and which can be applied with shear-sensitive gel consistency to, for example, topical or mucosal tissues.

It is an object of the present invention to overcome the prior art limitations and fill the need gap.

SUMMARY

A reversely thermo-reversible hydrogel composition of the present invention will desirably possess bioadhesive or mucoadhesive properties. Preferentially, the composition will be in the form of a gel or a liquid. Most preferably, the hydrogel composition will exist as a gel form or will be a liquid form that is capable of gelling upon contact with dermal or mucosal tissue.

In its broader sense, the present invention relates to a reversely thermo-reversible hydrogel composition comprising:
(a) A water soluble block copolymer comprising at least two blocks of polyethylene oxide and at least one block of polypropylene oxide; and
(b) At least one associative gelling adjuvant, said associative gelling adjuvant having a water solubility of less than 0.5 g/100 ml, preferably 0.3 g/100 ml, more preferably less than 0.1 g/100 ml at 20° C., and being capable of forming water soluble inter-molecular complexes with said water soluble block copolymers in water.

The present invention further relates to a reversely thermo-reversible hydrogel composition, having an adjustable sol-gel transition temperature in the range of from about 4-45° C., preferably from about 8-40 C.

The present invention further relates to a reversely thermo-reversible hydrogel composition, having a gel form in the temperature range of from about 4-50° C., preferably from about 8-45° C.

The present invention further relates to a hydrogel composition having improved flow and gelation characteristics with low solid content. The composition demonstrates excellent bioadhesion and is useful for a variety of pharmaceutical and cosmetic products and applications, and in particular, compositions useful topical and/or mucosal applications, such as esophageal, otic, vaginal, rectal, ophthalmic and treatments of disorders and imperfections of the skin.

The present invention also relates to reversely thermo-reversible hydrogel compositions having improved capability of solubilizing and/or stabilizing an effective amount of active ingredients sparingly soluble or insoluble in water.

The present invention also relates to reversely thermo-reversible hydrogel compositions having improved capability of dispersing and/or suspending otherwise insoluble active ingredients.

The present invention also relates to reversely thermo-reversible hydrogel compositions having improved bioadhesion and penetration of skin or skin appendages and is useful for treatment of skin or skin appendage related diseases.

The present invention also relates to reversely thermo-reversible hydrogel compositions having improved effectiveness and efficacy for treatment of skin or skin appendage related diseases.

The present invention also relates to reversely thermo-reversible hydrogel compositions useful in pharmaceutical and cosmetic products and applications for a controlled or sustained release of active ingredients.

Still, the present invention also relates to reversely thermo-reversible hydrogel compositions with improved aesthetics.

Thus the present invention further relates to a method and kits for preparing and delivering reversely thermo-reversible pharmaceutical and cosmetic hydrogel compositions for topical and/or mucosal applications, comprising the steps of preparing and providing a pharmaceutical and cosmetic hydrogel composition in the hydrogel vehicle, and applying the hydrogel composition to the mucous membranes. The hydrogel composition is applied to the topical and/or mucosal target, in an amount sufficient to deliver a non-toxic, pharmacologically effective amount of the pharmaceutical medicament and/or cosmetic active ingredient to the intended site of treatment and/or care/beauty for a controlled or sustained release of a variety of pharmaceutical medicaments and/or cosmetic active ingredients.

DETAILED DESCRIPTION

The present invention is related to a reversely thermo-reversible hydrogel composition, comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water.

The present invention is further related to reversely thermo-reversible hydrogel compositions, having an adjustable sol-gel transition temperature in the range of from about 4-45° C., preferably from about 8-40° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water.

The present invention is further related to reversely thermo-reversible hydrogel compositions, having an adjustable sol-gel transition temperature in the range of from about 4-45° C., preferably from about 8-40° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water, and an effective amount of at least one pharmaceutical medicament.

The present invention is further related to reversely thermo-reversible hydrogel compositions, having an adjustable sol-gel transition temperature in the range of from about 4-45° C., preferably from about 8-40° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water, and an effective amount of at least one cosmetic active ingredient.

The present invention is further related to reversely thermo-reversible hydrogel compositions, having an adjustable sol-gel transition temperature in the range of from about 4-45° C., preferably from about 8-40° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water, and an effective amount of at least one prophylactically or therapeutically anti-alopecia agent.

The present invention is further related to reversely thermo-reversible hydrogel compositions, having a gel form in the temperature range of from about 4-50° C., preferably from about 8-45° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water.

The present invention is further related to reversely thermo-reversible hydrogel compositions, having a gel form in the temperature range of from about 4-50° C., preferably from about 8-45° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water, and an effective amount of at least one pharmaceutical medicament.

The present invention is further related to reversely thermo-reversible hydrogel compositions, having a gel form in the temperature range of from about 4-50° C., preferably from about 8-45° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water, and an effective amount of at least one cosmetic active ingredient.

The present invention is further related to reversely thermo-reversible hydrogel compositions, having a gel form in the temperature range of from about 4-50° C., preferably from about 8-45° C., comprising a water soluble block copolymer comprising at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming water soluble inter-molecular complexes with said water soluble block copolymer in water, and an effective amount of at least one prophylactically or therapeutically anti-alopecia agent.

As used herein and in the appended claims, the term "gel" in reference to the present hydrogel compositions, means that the composition is a solid, jelly-like material that can have properties ranging from soft and weak to hard and tough. Gels are dilute systems, which exhibit no flow when in the steady-state.

Sol-gel or gel-sol transition temperature was observed as a gel melting temperature which was determined visually by the vial inversion method. The sample vials were immersed in an inverted position in a water bath and the temperature was decreased or increased slowly. The gel melting temperature was taken as the point where the gel started to flow.

By "reversely thermo-reversible" gel as that term is used herein, it is meant that the process of gelation takes place upon an increase in temperature rather than a decrease in temperature. This is counter-intuitive, since solution viscosity typically decreases with an increase in temperature.

By "use conditions" as that term is used herein it is meant all conditions to which the composition is likely to be exposed during its use, including during shipment and storage as well as during medical treatment or personal care.

The terms "pharmaceutically acceptable", "physiologically acceptable", and "cosmetically acceptable" and grammatical variations thereof, as used herein and in the appended claims as they refer to electrolytes (e.g., salts), bases, diluents, preservatives, buffers and other excipients, are used interchangeably and represent that the materials are capable of topical administration to human skin, esophagus, otic, vagina, rectum, or ophthalmus without the unacceptable production of undesirable physiological effects such as irritation, itching, stinging, or systemic effects such as nausea, dizziness, and the like.

The term "leave-on" type product as used herein and in the appended claims as they refer to the product is left on the skin upon application. Leave-on products are products like "anti-ageing cream", "body lotion/cream", "deodorants", and "hand lotion/cream". Whereas the term "rinse-off" type product as used herein and in the appended claims as they refer to the product that is rinsed-off shortly after application and use. Rinse-off products are products like "hair Shampoo", "hair conditioner", and "face washer".

All percentages mentioned herein are percentages by weight unless otherwise indicated.

Water Soluble Block Copolymer Comprising at Least Two Blocks of Polyethylene Oxide and at Least One Block of Polypropylene Oxide The terms "polyethylene oxide", "PEO", "EO", "polyethylene glycol", and "PEG" are used interchangeably to describe the present invention, and refer to synthetic polymer of ethylene oxide represented by the following chemical structure:

(1)

in which a is an integer representing the average number of monomer repeating units.

The terms "polypropylene oxide", "PPO", "PO", "polypropylene glycol", and "PPG" are used interchangeably to describe the present invention, and refer to synthetic polymer of propylene oxide represented by the following chemical structure:

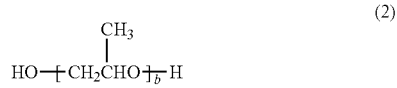

(2)

in which b is an integer representing the average number of monomer repeating units.

Block copolymer of polyethylene oxide and polypropylene oxide refers to a synthetic copolymer of polyethylene oxide block (Formula 1) and polypropylene oxide block (Formula 2), of varying molecular weights, and of various types, ranging from linear multi-block copolymers, side-chain grafted block copolymers, and hyper-branched block copolymers to star-shaped block copolymers; The block copolymers of polyethylene oxide and polypropylene oxide also comprise end-modified and chain-extended block copolymers of various types.

Of particular interest water soluble block copolymers of present invention are the block copolymers comprising at least two blocks of polyethylene oxide of the formula, $-[CH_2CH_2O]_a-$, and at least one block of polypropylene oxide of the formula, $-[CH_2CH(CH_3)O]_b-$, where a and b are each integers in the range of about 10-150, representing the average number of monomer repeating units in the polymer.

Exemplary water soluble block copolymers comprising at least two blocks of polyethylene oxide and at least at least one block of polypropylene oxide of present invention are tri-block copolymers commercially available under the trade name PLURONIC®, also known as Poloxamer from BASF Corporation, Mount Olive, N.J. A preferred Poloxamer polymers, having the general formula of $HO\text{-}(EO)_a(PO)_b(EO)_a\text{-}H$, are PLURONIC® F127 (also known as Poloxamer 407) with average values of a at about 101, and b at about 56, and PLURONIC® F 108 (also known as Poloxamer 338) with average values of a at about 141, and b at about 44, respectively.

Other exemplary water soluble block copolymers comprising at least two blocks of polyethylene oxide and at least one block of polypropylene oxide of present invention are the linear multi-block copolymer, having the general formula of $HO-[(PO)_b(EO)_a]_m(PO)_c[(EO)_a(PO)_b]_m-H$, where $(EO)_a$ is a polyethylene oxide block, and $(PO)_b$ or $(PO)_c$ is a polypropylene oxide block, a, b and c are each integers in the range of about 10-150, and m is the integer value greater than 0.

Other water soluble multi-block copolymers of present invention are chain extended, hyper-branded, or star-shaped block copolymers of the formula $\{[A(EO)_n(PO)_b(EO)_aA_n]E\}_m$, where $(EO)_a$ is a polyethylene oxide block, and $(PO)_b$ is a polypropylene oxide block, A is a monomer repeating unit, E is a chain extender or crosslinking agent, n is an integer ranging from 0 to 50, preferably 1 to 20 (0 to 20 in the case of non-biodegradable materials), even more preferably 2 to 16 (0 to 16 in the case of non-biodegradable materials), and m is the number of repeating units in the polymer molecule and is an integer equal to or greater than 2 (within practical limits, up to about 100,000 or more), preferably ranging from about 2 to about 500, more preferably about 3 to 100. Thus, where n is 0, the present invention contemplates polymers of the structure $\{[(EO)_a(PO)_b(EO)_a]E\}_m$.

Other water soluble block copolymer of present invention is an end-modified block copolymers of general formula $R\text{-}G\text{-}(EO)_n(PO)_b(EO)_a\text{-}G\text{-}R$, where $(EO)_a$ is a polyethylene oxide block, and $(PO)_b$ is a polypropylene oxide block, G is selected from a group consisting of C—C, C—O, C(O)NH, S—C. C(O)—O, and Si—O, R is alkyl or arylalkyl with alkyl chain length in the range of $C_6\text{-}C_{36}$, a is an integer ranging from 50 to 150, b is an integer ranging from 35 to 70.

Exemplary water soluble block copolymers are the alkyl or arylalkyl end-modifiers block copolymers comprising at least two blocks of polyethylene oxide and at least one block of polypropylene oxide, which are a product of alcohol condensation reactions with a terminal alkyl or arylalkyl group. The alkyl group should have hydrophobic character, such as butyl, hexyl and the like. An alkyl poloxamer may have the general formula $R\text{-}[(EO)_a(PO)_b(EO)_a]_m\text{-}R'$, where $(EO)_a$ is a polyethylene oxide block, $(PO)_b$ is a polypropylene oxide block, R and R' are the nonpolar pendant groups, such as alkyl and arylalkyl with alkyl chain length in the range of $C_6\text{-}C_{36}$, and m is an integer ranging from 1-10.

Other exemplary water soluble block copolymers of present invention are the grafted block copolymers comprising grafted side chain of at least two blocks of polyethylene oxide and at least one block of polypropylene oxide, having general formula of $[A(EO)_a(PO)_b(EO)_a]_m$, where $(EO)_a$ is a polyethylene oxide block, $(PO)_b$ is a polypropylene oxide block, a and b are each integers in the range of about 10-150. A is a repeat unit of backbone of the copolymers consisting of vinyl, ester, amide, imide, ether, siloxane linkages, and the like, m is the number of repeating units in the polymer molecule and is an integer equal to or greater than 2.

Other water soluble multi-block copolymers of present invention are polyester chain extended block copolymers of the formula $\{[A_n(EO)_a(PO)_b(EO)_aA_n]E\}_m$, where $(EO)_a$ is a polyethylene oxide block, $(PO)_b$ is a polypropylene oxide block, A is a monomer repeating unit, $(EO)_a$ is a polyethylene oxide block, and $(PO)_b$ is a polypropylene oxide block as previously defined, E is a chain extender or crosslinking agent, n is an integer ranging from 0 to 50, preferably 1 to 20 (0 to 20 in the case of non-biodegradable materials), even more preferably 2 to 16 (0 to 16 in the case of non-biodegradable materials) and m is the number of repeating units in the polymer molecule and is an integer equal to or greater than 2 (within practical limits, up to about 100,000 or more), preferably ranging from about 2 to about 500, more preferably about 3 to 100. Thus, where n is 0, the present invention contemplates polymers of the structure $\{[(EO)_a(PO)_b(EO)_a]E\}_m$.

The monomer repeating units which may be derived from an aliphatic hydroxy carboxylic acid or a related ester, lactone, dimeric ester, carbonate, anhydride, dioxanone, amide, or related monomer, and preferably derived from an aliphatic α-hydroxy carboxylic acid or related ester, such units derived from the following: including, for example, lactic acid, lactide, glycolic acid, glycolide, or a related aliphatic hydroxyl carboxylic acid, ester (lactone), dimeric acid or related compound such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures thereof. The use of α-hydroxyacids and their corresponding cyclic dimeric esters, especially lactide, glycolide, and caprolactone in the present invention, is preferred. It is noted that in using certain of the described monomers according to the present invention, the monomeric units which are produced are not specifically ester groups, but may include such groups as carbonate groups (polycarbonates), amino acids (which produce polyamides) and related groups which are derived from the above-described monomers or which contain a nucleophilic group and an electrophilic group and can be polymerized. It will be understood that the term polyester shall encompass polymers which are derived from all of the above monomers, with those which actually produce ester units being preferred.

The terms "poly(hydroxy carboxylic acid)" or "poly($\alpha$-hydroxy carboxylic acid)" are terms used to describe certain polyester A blocks of the $\{[A_n(BCB)A_n]E\}_m$ multiblocks used in polymeric compositions according to the present invention where A is a polymeric polyester unit derived from an aliphatic hydroxy carboxylic acid or a related ester or dimeric ester and is preferably derived from an aliphatic $\alpha$-hydroxy carboxylic acid or related ester, including a cyclic dimeric ester, such as, for example, lactic acid, lactide, glycolic acid, glycolide, or a related aliphatic hydroxycarboxylic acid or ester (lactone) such as, for example, $\epsilon$-caprolactone, $\delta$-glutarolactone, $\delta$-valerolactone, $\gamma$-butyrolactone and mixtures, thereof, among numerous others as set forth herein. The use of $\alpha$-hydroxyacids and their corresponding cyclic dimeric esters, especially lactide and glycolide in the present invention, is preferred.

Other suitable end-modified components may include, but are not limited to, ionizable polymers. The ionizable polymers of the present invention include linear, branched and/or crosslinked polymers. Of particular interest are carboxyvinyl polymers of monomers such as acrylic acid, methacrylic acid, ethacrylic acid, phenyl acrylic acid, pentenoic acid and the like. Poly(acrylic acid) and its salts is a preferred carboxyvinyl polymer. One or more poly(carboxyvinyl) polymers may be used in the polyoxyalkylene composition of the present invention. Copolymers, such as by way of example only, copolymers of acrylic acid and methacrylic acid, are also contemplated.

Preferably, the reversely thermo-reversible hydrogel composition of the present invention can include from approximately 5% to 20%, preferably from 8% to 18%, more preferably from 10% to 15% by weight of a water soluble block copolymer comprising at least two blocks of polyethylene oxide and at least one block of polypropylene oxide.

Needless to say, a person skilled in the art will take care to select the appropriate water soluble block copolymer, comprising at least two blocks of polyethylene oxide and at least one block of polypropylene oxide, such that the advantageous properties of the hydrogel composition according to the present invention are not, or are not substantially, adversely affected.

Associative Gelling Adjuvant

The term "associative gelling adjuvant" refers to a selected group of agents that modifies the gelling effect of other gelling agents while having few if any direct effects when given by themselves. By nature, the associative gelling adjuvants themselves have very limited water solubility, and typically have a water solubility of less than 0.5 g/100 ml, preferably less than 0.3 g/100 ml, more preferably less than 0.1 g/100 ml at 20° C., and are not capable of viscosifying or gelling water when they are present in water by themselves.

With the currently commercially available Poloxamer polymers, the ability to obtain a sol-gel transition at desired lower temperature than the room temperature is limited while maintaining polymers at relatively low concentration. At the same time with a low solid content in the composition, it is crucial for the system to be able to carry and stabilize an effective amount of active ingredients for a controlled and sustained release of active ingredients.

For example, about 20% w/w Pluronic® F 127 in water is needed to have a sol-gel transition temperature at about 25° C. To extend the sol-gel transition temperature far below 25° C., a higher concentration of block copolymer has to be used. In fact, as high as 35% w/w Pluronic® F 127 is needed to have a sol-gel transition temperature at about 8° C. In contrast, only about 18.5% Pluronic® F 127 in combination with about 8% laureth-4 are needed to have the same sol-gel transition temperature. Due to the much reduced polymer concentration, solution viscosity is much lower, and resulting hydrogel is less tacky, much less residue, better shear sensitive property and cosmetic effects.

In accordance with aspects of the present invention, it has been surprisingly discovered that the gelling efficiency of water soluble block copolymers, comprising at least two blocks of polyethylene oxide and at least one block of polypropylene oxide, has been largely improved by addition of small amount of at least one associative gelling adjuvant. It has been discovered that although the relative amount of polymers used to form reversely thermo-reversible gel at desired temperature has been largely reduced, the resulting hydrogel compositions have improved capability of solubilizing and/or stabilizing an effective amount of pharmaceutical medicaments and cosmetic active ingredients that are sparingly soluble or insoluble in water.

It has been also surprisingly discovered that the sol-gel transition temperatures of such reversely thermo-reversible hydrogel compositions, comprising block copolymers comprising at least two blocks of polyethylene oxide and at least one block of polypropylene oxide, of present invention can be regulated over a relatively wide temperature ranges under use conditions by incorporating an effective amount of at least one associative gelling adjuvant. The ability to adjust the sol-gel transition temperature of the hydrogel compositions over a wide temperature range of use conditions with relatively low polymer concentration overcomes the limitations of prior art and is important and very useful wherever it is desirable in a liquid state or gel form from either a performance or handling point of view. In particular, the present invention provides pharmaceutical, cosmetic and personal care compositions, having the properties set forth above, for the delivery of an effective amount of active ingredients with controlled or sustained release.

While not wishing to be bound by any particular theory it is proposed herein that the inter-molecular interactions, such as hydrogen bonding interaction, between the associative gelling adjuvant and the water soluble block copolymer, comprising at least two blocks of polyethylene oxide and at least one block of polypropylene oxide, result in the formation of water soluble inter-molecular complexes, which are responsible for the observation of enhanced gelling efficiency of present invention.

Examples of the associative gelling adjuvant, include, but are not limited to, oxyalkylated fatty alcohol, esters of oxyalkylated fatty alcohol, oxyalkylated alkyl alcohol, esters of oxyalkylated alkyl alcohol; oxyalkylated alkylaryl alcohol, aliphatic hydroxy carboxylic acid, ester of aliphatic hydroxy carboxylic acids, aromatic hydroxy carbolic acid esters of aromatic hydroxy carbolic acid, poly(hydroxy carboxylic acid), oxyalkylated sorbitan esters, oxyalkylated triglycerides, oxyalkylated glyceryl esters, esters of oxyalkylated sorbitol, polyol esters, sorbitan ester and the like.

Suitable associative gelling adjuvants for use herein include, but not limited to, laureth-2, laureth-3, laureth-4, laureth-5, laureth-6, and the like; Oleth-2, Oleth-5, Oleth-10, and the like; $C_{12-13}$ pareth-2, $C_{12-13}$ pareth-3, $C_{12-13}$ pareth-4, $C_{12-13}$ pareth-5, $C_{12-13}$ pareth-6, and the like; di-PPG-2 myreth-9 adipate, di-PPG-2 myreth-10 adipate, di-PPG-2 myreth-11 adipate, and the like; salicylic acid and its derivatives; and the like.

An important aspect of the present invention is that the sol-gel transition temperature of the hydrogel compositions can be regulated in the temperature range of from about 4-45° C., preferably from about 8-40° C., meanwhile having a sol-gel transition temperature greater than 45° C., by adjusting relative ratio of the water soluble block copolymer to the associative gelling adjuvant at relatively low polymer concentration. Such ability of adjusting the sol-gel transition temperature of the hydrogel composition overcome the limitations of prior art and is important and very useful wherever it is desirable in a fluid or a gel state from either performance or handling point of view.

Preferably, the reversely thermo-reversible hydrogel composition of the present invention can include from approximately 0.1% to 12%, preferably from 0.5% to 10%, more preferably from 1% to 8% by weight of at least one associative gelling adjuvant, said associative gelling adjuvant having a water solubility of less than 0.5 g/100 ml, preferably less that 0.3 g/100 ml, more preferably less than 0.1 g/100 ml, and being capable of forming water soluble inter-molecular complexes with said water soluble block copolymers in water.

Preferentially, the hydrogel composition will be in the form of a gel or a liquid. Most preferably, the hydrogel composition will exist as a gel or will be a liquid that is capable of gelling upon contact with dermal or mucosal tissue.

For some applications, the practical advantage of such reversely thermo-reversible hydrogel composition is that the formulation can be administered as a flowing liquid at ambient temperatures. Upon contact with body tissues it gels, thus changing its flow properties, and more importantly, its clearance from the site of application is dramatically reduced.

For some other applications, the practical advantage of such reversely thermo-reversible hydrogel composition is that the formulation can be administered as a gel at ambient temperature. The low solid content of hydrogel composition of present invention possesses a shear-sensitive characteristic and can be easily applied with dermal or mucosal tissue, and remains on the site for a prolonged period of time for the controlled or sustained release of active ingredients.

The gel state of the hydrogel composition of present invention not only facilitates the administration of the formulation in some desired applications but also help to solubilize and/or stabilize sparely soluble or insoluble active ingredients. For example, the use of Salicylic acid or its derivatives for treating dandruff, acne, skin wrinkling, skin pigmentation, warts, freckles, or skin-related problems is well known in the preparation of dermatologic and cosmetic formulations. Salicylic acid or its derivatives are usually in crystalline form and are not sufficiently soluble in water or oils traditionally used in dermatological and cosmetic preparations. Typical problems which occur when using Salicylic acid or its derivatives in making dermatologic and cosmetic products are that the Salicylic acid or its derivatives tend to crystallize out within various compositions, which significantly reduces the bioavailability of Salicylic acid or its derivatives for treating or preventing the aforementioned skin problems. The hydrogel composition of present invention not only help to solubilize sparely soluble salicylic acid and its derivatives, the gel state of hydrogel composition also prevents Salicylic acid or its derivatives from crystallize out within the compositions which significantly increase the bioavailability of Salicylic acid or its derivatives for treating or preventing the aforementioned skin problems.

From process point of view, a composition may be prepared at low temperatures while the composition is in a low viscosity state. Mixing of ingredients under low viscosity is expected to be easier, thus simplifying the manufacturing process.

The hydrogel compositions of present invention exhibit many advantages. Due to the improved gelling efficiency at desired temperature range of physiologically appropriate use conditions at relatively low polymer concentration, they form clear and transparent gel and possess the appropriate thickness, emolliency, and cosmetic effect with a minimum of solids content. The hydrogel composition of the present invention remains clear and transparent before and after the triggering environmental change. In addition, very little residue is formed upon dehydration after application which may be important in some applications. Furthermore, the hydrogel compositions have improved capability of solubilizing and/or stabilizing for otherwise insoluble additives. It has been discovered that a wide variety of useful pharmaceuticals medicaments and cosmetic active ingredients which are not ordinarily soluble in water can in fact be dissolved and/or stabilized and/or dispersed and/or suspended in the hydrogel compositions of the present invention. In many circumstances, an alcohol free hydrogel composition can be formulated due to the enhanced solubilizing and/or stabilizing ability of hydrogel composition of the present invention. In some instances, the addition of other auxiliary solubilizers/compatibilizers was found to be helpful. However, the critical desired sol-gel transition temperature is maintained.

The present invention is further related to a method for preparing the hydrogel composition, comprising the steps of:
(a) Dissolving the said water soluble block copolymer in water at the temperature below 20° C., and
(b) Then mixing the dissolved copolymer with at least one associative gelling adjuvant at a suitable temperature to form a reversely thermo-reversible hydrogel composition.

Needless to say, a person skilled in the art will take care to select the appropriate associative gelling adjuvants that are capable of forming water soluble inter-molecular complexes with water soluble block copolymer, comprising at least two blocks of polyethylene oxide and at least one block of polypropylene oxide, such that the advantageous properties of the hydrogel composition according to the present invention are not, or are not substantially, adversely affected.

Pharmaceutical Medicament

As those skilled in the art will appreciate, the hydrogel compositions of the present invention may be utilized as drug delivery vehicles for administering a variety of pharmaceutical drugs, and diagnostic compounds.

Suitable pharmaceutical drugs and diagnostic compounds for incorporating into the hydrogel drug delivery compositions of the present invention can be water soluble, water sparely soluble and insoluble pharmaceutical compounds. Exemplary pharmaceutical drugs, therapeutic agents or diagnostic agents which can be administered by the hydrogel compositions of the present invention include, but are not limited to:

(1) Antibacterial substances such as beta-lactam antibiotics, such as cefoxitin, n-formamidoyl-thienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin, sulfonamides; aminoglycoside antibiotics such as gentamycin, kanamycin, amikacin, sisomicin and tobramycin; nalidixic acid and analogs such as norfloxacin and the antimicrobial combination of flucalanine/pentizidone; nitrofurazones, and the like;

(2) Antihistaminics and decongestants such as pyrilamine, chlorpheniramine, tetrahydrazoline, antazonline, and the like;

(3) Anti-inflammatories such as cortisone, hydrocortisone, hydrocortisone acetate, betamethasone, dexamethasone, dexamethasone sodium phosphate, prednisone, methylpredinisolone, medrysone, fluorometholone, fluocortolone, prednisolone, prednisolone sodium phosphate, triamcinolone, indomethacin, sulindac, its salts and its corresponding sulfide, and the like;

(4) Miotics and anticholinergics such as echothiophate, pilocarpine, physostigmine salicylate, diisopropylfluorophosphate, epinephrine, dipivolyl epinephraine, neostigmine, echothiophate iodide, demecarium bromide, carbachol, methacholine, bethanechol, and the like;

(5) Mydriatics such as atropine, homatropine, scopolamine, hydroxyamphetamine, ephedrine, cocaine, tropicamide, phenylephrine, cyclopentolate, oxyphenonium, eucatropine, and the like; and other drugs used in the treatment of eye conditions or diseases such as (6) Antiglaucoma drugs, for example, betaxalol, pilocarpine, timolol, especially as the maleate salt and R-timolol and a combination of timolol or R-timolol with pilocarpine. Also included are epinephrine and epinephrine complex or prodrugs such as the bitartrate, borate, hydrochloride and dipivefrin derivatives and hyperosmotic agents such as glycerol, mannitol and urea;

(7) Antiparasitic compounds and/or anti-protozoal compounds such as ivermectin; pyrimethamine, trisulfapyrimidine, clindamycin and corticosteroid preparations;

(8) Antiviral effective compounds such as acyclovir, 5-iodo-2'-deoxyuridine (IDU), adenosine arabinoside (Ara-A), trifluorothymidine, and interferon and interferon inducing agents such as Poly I:C;

(9) Carbonic anhydrase inhibitors such as acetazolamide, dichlorphenamide, 2-(p-hydroxyphenyl) thio-5-thiophenesulfonamide, 6-hydroxy-2-benzothiazolesulfonamide and 6-pivaloyloxy-2-benzothiazolesulfonamide;

(10) Anti-fungal agents such as clotrimzole, fluconazole, flucytosine, itraconazole, ketoconazole, miconazole, ciclopirox, econazole, nystatin, oxiconazole, terbinafine Hydrochloride, tioconazole, butoconazole, terconazole, miconazole nitrate, metronidazole, isoconazole nitrate, and tolnaftate;

(11) Anesthetic agents such as etidocaine cocaine, henoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

(12) Ophthalmic diagnostic agents such as: (a) Those used to examine the retina and chloride-sodium fluorescein; (b) Those used to examine the conjunctive, cornea and lacrimal apparatus such as fluorescein and rose bengal; and (c) Those used to examine abnormal pupillary responses such as methacholine, cocaine, adrenaline, atropine, hydroxyamphetamine and pilocarpine;

(13) Ophthalmic agents used as adjuncts in surgery such as alphachymotrypsin and hyaluronidase;

(14) Chelating agents such as ethylenediamine tetraacetate (EDTA) and deferoxamine;

(15) Immunosuppressive agents and anti-metabolites such as methotrexate, cyclophosphamide, 6-mercaptopurine, and azathioprine;

(16) Peptides and proteins such as atrial natriuretic factor, calcitonin-gene related factor, lutinizing hormone, releasing hormone, neuroterisin, vasoactive intestinal peptide, vasopressin, cyclosporine, Botulinum toxin, interferon, substance P enkephalins, epidermal growth factor, eyederived growth factor, fibronectin, insulin-like growth factor and mesodermal growth factor,

(17) Acne treatment agents, such as salicylic acid and its derivatives, sulfur, lactic acid, glycolic, pyruvic acid, azelaic acid, benzoyl peroxide, urea, resorcinol and N-acetylcysteine, and retinoids, such as retinoic acid, and its derivatives, and the like;

(18) Lubricating agents such as sodium hyaluronate or polyvinyl alcohol; and

(19) Combinations of the above such as antibiotic/anti-inflammatory as in neomycin sulfate-dexamethasone sodium phosphate, concomittant anti-glaucoma therapy such as timolol maleate-aceclidine.

As those skilled in the art will appreciate, the foregoing listing of pharmaceutical compounds is exemplary only. Because the drug delivery compositions of the present invention are uniquely suited for utilization in a wide variety of physiological applications such as the ocular, oral, nasal, rectal or subcutaneous administration of pharmaceutical compounds, a wide variety of pharmaceutical medicaments may be incorporated therein. Accordingly, the foregoing listing of pharmaceutical medicaments is not intended to limit the scope of the present invention and is exemplary only.

The hydrogel compositions of present invention are most suitable for the pharmaceutical drugs which exhibit poor bioavailability, such as levobunolol, pilocarpine, dipivefrin and others.

Preferably, when utilized as an hydrogel drug delivery vehicle for topical application, drop instillation, oral administration or injection, the hydrogel compositions of the present invention can be modified to include from approximately 0.0001% to 70%, preferably 0.001% to 50%, by weight pharmaceutical drugs or diagnostic agent. To prepare a hydrogel drug delivery vehicle in accordance with the teachings of the present invention, an appropriately effective amount of the pharmaceutical compound of choice is simply incorporated into the hydrogel composition at the composition formulation temperatures and pHs. Preferably, the compound of choice will be soluble in the solution or will be homogeneously dispersed. Soluble pharmaceutical compounds will readily dissolve in the hydrogel composition, whereas insoluble compounds will preferably be pulverized for even dispersion throughout the hydrogel compositions.

Along these lines, it is also contemplated as being within the scope of the present invention to incorporate insoluble or erodible micro-particulate drug delivery systems such as those known in the art into the hydrogel compositions. In this manner, controlled release drug delivery systems can be incorporated into the hydrogel compositions of the present invention and retained in position when administered by drop or injection.

In some embodiments, the hydrogel compositions may comprise traditional Chinese herb medicines or Chinese herb extracts. The traditional Chinese herb medicines may be pulverized, uniformly dispersed and/or suspended in the hydrogel composition. The hydrogel compositions may serve not only as an effective dispersion and/or suspension medium as drug delivery vehicles but also are capable of extracting the herb actives from the various traditional Chinese herb medications.

Pharmaceutically acceptable excipients that can be included in the pharmaceutical hydrogel compositions of the present invention include, but not limited to, for example, physiologically tolerable surfactants, solvents, humectant, emollients, penetration enhancer, colorants, fragrances, and the like, which are well known in the art, and some of them are described in the context later. The hydrogel compositions preferably have a pH value in the range of about 1 to about 12. Other preferred embodiments may have a pH value in the range of about 3.5 to about 10.

A discussion of particular pharmaceutical applications and formulations follows.

Esophageal, oral cavity and buccal applications: The hydrogel composition provides a suitable vehicle for delivering drugs within the esophageal lining; Ophthalmic applications: Hydrogel formulation of present invention can be applied as drops which gel upon contact with eye or as a shear sensitive gel. Since gelling can be accomplished with low concentrations of the polymer, blurring can be minimized upon drop instillation; Nasal applications: Hydrogel formulation composition can be readily sprayed at low temperature; the subsequent gelation occurs only after administration of the formulation and only at the site of application; Vaginal/rectal applications: The hydrogel will increase the residence time of formulations, and prevent the leak-back that is typical undesired effect of current formulations.

Veterinary applications: The reversely thermo-reversible hydrogel composition of the present invention also may be useful in the treatment of not only human conditions but in providing treatments for animal care. For veterinary products, hydrogel composition is indicated for the preparation of topical dermal products, such as antibacterials, antifungals, antipruritics, and antiseborrhea, antiodor, and antiseptic/wound healing preparations. Otic products would include ear cleansers with or without actives, such as, antifungals. Ophthalmic products would include eye moisturizers or antimicrobial preparations.

Tablet excipients or gel capsules: The hydrogel composition of the present invention may be introduced in powder form into the tablet along with the active ingredients and other ingredients. The hydrogel composition along with active ingredients and other ingredients also can be encapsulated.

Injectibles: A depot formulation may be prepared and administered at low viscosity to a subdermal or intramuscular site, which will slowly release the active ingredient for a sustained or extended period; alternatively, the hydrogel composition of the present invention may be prepared in a gel form in order to suspend microspheres or particles in the formulation. The formulation can then take advantage of the shear thinning properties of the hydrogel composition. Thus, during injection, the formulation is subjected to shear stresses which reduce viscosity and allow an ordinarily viscous formulation to be introduced into the patient by injection. Cessation of the strain results in reestablishing the high viscosity of the gel form of the formulation, so that the active agent may be slowly released therefrom.

Preparation of pharmaceutic compositions may be accomplished with reference to any of the pharmaceutic formulation guidebooks and industry journals which are available in the pharmaceutic industry. These references supply standard formulations which may be modified by the addition or substitution of the reversely thermo-reversible hydrogel composition of the present invention into the formulation. Suitable guidebooks include Pharmaceutics and Toiletries Magazine, Vol. 111 (March, 1996); Formulary: Ideas for Personal Care; Croda, Inc, Parsippany, N.J. (1993); and Pharmaceuticon: Pharmaceutic Formulary, BASF, which are hereby incorporated in their entirety by reference.

The pharmaceutical composition may be in any form. Suitable forms will be dependent, in part, of the intended mode and location of application. Ophthalmic and otic formulations are preferably administered in droplet or liquid form; nasal formulations are preferable administered in droplet or spray form, or may be administered as a powder (as a snuff); vaginal and rectal formulations are preferably administered in the form of gel or thick liquid; veterinary formulations may be administered as a gel, liquid, cream, lotion, or spray; esophageal and buccal/oral cavity applications are preferably administered from solution or as a powder; film forming applications or dermal applications may be administered as a liquid, cream, lotion, soft gel, hard gel sticks, roll-ons formulations or pad-applied formulations.

Exemplary drugs or therapeutics delivery systems which may be administered using the hydrogel composition of the present invention include, but are in no way limited to, mucosal therapies, such as esophageal, otic, rectal, buccal, oral, vaginal, and urological applications; topical therapies, such as wound care, skin care and teat dips; and intravenous/subcutaneous therapies, such as intramuscular, intrabone (e.g., joints), spinal and subcutaneous therapies, tissue supplementation, adhesion prevention and parenteral drug delivery. In addition, further applications include transdermal delivery and the formation of depots of drug following injection. The pharmaceutical medicaments is most suitable absorbable through skin or mucosal membranes.

The present invention is further related to a method for preparing pharmaceutical hydrogel compositions, comprising the steps of:
(a) Dissolving the said water soluble block copolymer in water at the temperature below 20° C.,
(b) Then mixing the dissolved copolymer with other excipients and/or at least one effective amount of pharmaceutical medicament or diagnostic compound at a suitable temperature to substantially dissolve or disperse uniformly the pharmaceutical medicament or diagnostic compound in the aqueous solution, and
(c) Finally mixing the dissolved copolymer with at least one associative gelling adjuvant at a suitable temperature to form a reversely thermo-reversible pharmaceutical and/or diagnostic hydrogel composition.

Prophylactic or Therapeutic Anti-Alopecia Agent

As those skilled in the art will appreciate, the hydrogel compositions of the present invention may be utilized as delivery vehicles for administering a variety of prophylactic or therapeutic anti-alopecia agent.

According to aspects of present invention, the reversely thermo-reversible hydrogel composition can further comprises at least one prophylactic or therapeutic anti-alopecia agent. Examples of prophylactic or therapeutic anti-alopecia agents include, but are not limited to, benzalkonium chloride, benzethonium chloride, phenol, estradiol, diphenhydramine hydrochloride, chlorpheniramine maleate, chlorophyllin derivatives, cholesterol, salicylic acid or its derivatives, p-hydroxy benzoic acid or its ester derivatives, acetaminophen, Ibuprofen, cystine, red pepper tincture, benzyl nicotinate, dl-menthol, peppermint oil, calcium pantothenate, panthenol, castor oil, hinokitiol, prednisolone, resorcinol, minoxidil, cromakalin, pinacidil, naminidil, diphenylcyclopropenone, tricomin, antiandrogen agents such as cyproterone acetate, danazol and flutamide, 5-alpha reductase inhibitors such as finasteride, turosteride, LY-191704, MK-306 and dutasteride (U.S. Pat. No. 4,377,584), and those compounds selected from the classes of s-triazines, benzopyrans, pyridinopyrans and thiane-1-oxides or pharmaceutically acceptable salts or derivatives of any one of the aforementioned, and the like.

Suitable prophylactic or therapeutic anti-alopecia agent for use herein include, but not limited to, salicylic acid and its derivatives, p-hydroxy benzoic acid and its derivatives, dl-menthol, minoxidil, flutamide, finasteride, and the like.

As those skilled in the art will appreciate, the foregoing listing of prophylactic or therapeutic anti-alopecia agent is exemplary only. Because the hydrogel compositions of the present invention are uniquely suited for utilization in treating and/or preventing alopecia and restoring and/or promoting hair growth.

The anti-alopecia hydrogel composition of present invention is broadly applicable to baldness in general, the above defined reversely thermo-reversible hydrogel composition may be especially useful for the treatment of androgenetic alopecia. It has been postulated that an accumulation of materials such as 5-a-dihydro testosterone, a tissue active androgen, in some scalp hair follicles over time causes the regression of hair growth in such follicles. Without being bound by any theory of operation, it is believed that local application of said hydrogel composition of present invention to the skin of the affected area which has been shown to result in renewed growth of hair, may remove excess androgen or clear up the hair follicles.

The applicant has now found that the reversely thermo-reversible hydrogel composition comprising at least one prophylactically or therapeutically anti-alopecia agent resulted surprisingly in an markedly improved induction and stimulation of the hair growth and an action on the retardation of hair loss, as well as a marked increase in cutaneous bioavailability and/or transcutaneous penetration.

The reversely thermo-reversible hydrogel composition has been found to have an activity which is superior whenever employed either as a leave-on type hydrogel composition or rinse-off type hydrogel shampoo composition on the scalp for treating and/or preventing alopecia and restoring and/or promoting hair growth. The reversely thermo-reversible hydrogel composition of the present invention may be applied topically to the affected area of the scalp at least once a day for a period of three months in an amount of from about 0.01 ml to about 5 ml, preferably about 0.05 ml to about 3.5 ml. The superiority of the present invention is that the anti-alopecia hydrogel composition may be applied to the affected area of scalp, remains for about 1-2 minutes, and then rinsed or washed off just like a shampoo. This makes it possible for the treatment to achieve an equivalent or superior effectiveness in comparing with other leave-on type anti-alopecia compositions in prior art.

Preferentially, the reversely thermo-reversible hydrogel composition will be in the form of a gel or a liquid. Most preferably, the reversely thermo-reversible hydrogel composition will exist as a gel or will be a liquid that is capable of gelling upon contact with the scalp.

Preferably, the hydrogel compositions of the present invention can include from approximately 0.01% to 50%, preferably from 0.05% to 30%, more preferably from 0.1% to 15% by weight of the prophylactic or therapeutic anti-alopecia agent. To prepare a hydrogel composition in accordance with the teachings of the present invention, an effective amount of prophylactic or therapeutic anti-alopecia agent of choice is simply incorporated into the hydrogel composition at the composition formulation temperatures and pHs. Preferably, the prophylactic or therapeutic anti-alopecia agent of choice will be soluble in the hydrogel or will be homogeneously dispersed.

The present invention is further related to a method for preparing topical anti-alopecia reversely thermo-reversible hydrogel compositions, comprising the steps of:
(d) Dissolving the said water soluble block copolymer in water at the temperature below 20° C.,
(e) Then mixing the dissolved copolymer with other excipients and/or at least one effective amount of prophylactic or therapeutic anti-alopecia agent at a suitable temperature to substantially dissolve or disperse uniformly in the aqueous solution, and
(f) Finally mixing the dissolved copolymer with at least one associative gelling adjuvant at a suitable temperature to form a topical reversely thermo-reversible hydrogel composition for the treatment of hair loss.

The present invention further relates to a method for treating and/or preventing alopecia and restoring and/or promoting hair growth said method comprising applying said reversely thermo-reversible hydrogel composition topically to the scalp by means of aerosol, spray, pump pack, brush, swab, or other applicator for the dosing followed by massaging sufficiently to cause said composition to penetrate the skin so as to contact the hair follicles, followed by either leaving the composition on the scalp or rinsing the composition off from the scalp shortly after application.

Cosmetic Active Ingredients

As those skilled in the art will appreciate, the hydrogel compositions of the present invention may further comprise about 0.01-70%, preferably about 0.1-50%, by weight of the total composition of cosmetic active ingredients. The cosmetic may be skincare products such as facial hydrogel, hands and foot care hydrogels; acne treatment hydrogel, shaving hydrogel, cleansing hydrogel; antiperspirant; hair remover hydrogel, tooth whitening hydrogel, color makeup products such as makeup base, hydrogel foundation, eye shadow, eyeliner, blush; sun screen hydrogel; insect repellant and the like.

Suitable cosmetic active ingredients for incorporating into the hydrogel compositions of the present invention can be essential oils, moisture retention agents, skin-beautifying agents, sun screen, antiperspirants, vitamins, amino acids, anti-acne agents, antiseptics or antibacterial agents, zinc salts, tooth whitening agents, depilatory agents, fragrance oils, insect repellants, antioxidants, chelating agents, refrigerants, anti-inflammatory agents, salts, colorants, particulate fillers. Exemplary cosmetic active ingredients which can be incorporated into the hydrogel compositions of the present invention include, but are not limited to:

(1) Essential oils include, but are not limited to, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, tea tree oil and tangerine oil. Alternatively, the present invention provides for the use of active agents found in essential oils such as, but not limited to, 1-citronellol, $\alpha$-amyl-cinnamaldehyde, lyral, geraniol, farnesol, hydroxy-citronellal, isoeugenol, eugenol, eucalypus oil and eucalyptol, lemon oil, linalool, and citral. Apart from their effects as fragrances or flavorants, such compounds also may be useful in the instant invention as antimicrobial agents. The concentrations of essential oils or isolated components may be between about 0.3 and 1 wt. % or between about 0.1 and 0.5 wt. % or between 0.5 and 2 wt. %.

(2) Moisture retention agents include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside, and the like;

(3) Skin-beautifying agents include whitening agents such as placenta extract, arbutin, glutathione and Yukinoshita extract, kojic acid, placenta extract, sulfur, ellagic acid, linoleic acid, tranexamic acid; cell activators, such as royal jelly, photosensitizers, cholesterol derivatives, calf blood extract, $\alpha$-hydroxy acid and $\beta$-hydroxy acid; rough and dry skin improvers; blood circulation improvers, such as nonylic acid vanillyl amide, benzyl nicotinate, $\beta$-butoxyethyl nicotinate, capsaicin, zingerone, cantharis tincture, ichtammol, caffeine, tannic acid, $\alpha$-borneol, tocopheryl nicotinate, inositol hexanicotinate, cyclandelate, cinnarizine, tolazoline, acetyl choline, verapamil, cepharanthin and $\gamma$-oryzanol; skin astringents, such as zinc oxide and tannic acid; and anti-seborrheic agents, such as sulfur and thianthol; and skin colorants such as $\alpha$-hydroxy-acetone, and the like;

(4) Sun screen include UV absorbents of benzoate type, such as p-aminobenzoic acid, ethyl dihydroxypropyl p-aminobenzoate, glyceryl p-aminobenzoate, and octyl p-dimethylaminobenzoate; anthranilic acid type UV absorbents such as methyl anthranilate; UV absorbents of salicylic acid type, such as methyl salicylate, octyl salicylate, and triethanol amine salt or salicylic acid; cinnamic acid type UV absorbents, such as octyl p-methoxycinnamate, diethanol amine salt of p-methoxyhydroxycinnamic acid, and dimethocycinnamic acid/isooctanoic acid gryceride; benzophenone type UV absorbents, such as 2,4-dihydroxybenzophenon, 2,2',4,4'-tetrahydroxybenzophenon, 2-hydroxy-4-methyoxybenzophenon, 2-hydroxy-4-methoxypenzophenon-5-sulfonic acid, 2,2'-dihydroxy-4-methoxypenzophenon, and 2-hydroxy-4-N-octoxybenzophenon; UV absorbents of urocanic acid type, such as ethyl urocanate; UV absorbents of dibenzoylmethane type, such as 4-tert-butyl-4'-methoxy-dibenzoylmethane, 4-isopropyl dibenzoylmethane; 3-(4-methylbenzylidene) camphor, octyltriazone, e-ethylhexyl-2-cyano-3,3-diphenylacrylate, 2-phenyl-benzoimidasole-5-sulfate, 4-(3,4-dimethoxypnehylm-ethylene)-2,5-dioxo-1-imidazolidine, and 2-ethylhex-ylpropionate. The UV absorber may be encapsulated in a polymer powder. The aforesaid powders which absorb or scatter UV ray may be used, for example, titanium oxide fine powder, fine powder of titanium oxide containing iron, zinc oxide fine powder, cerium oxide fine powder and a mixture thereof, and the like;

(5) Antiperspirant include aluminum chlorohydrate, aluminum chloride, aluminum sesquichlorohydrate, zirconyl hydroxy chloride, aluminum zirconium hydroxychloride and aluminum zirconium glycine, and the like;

(6) Vitamins include vitamin A such as vitamin A oil, retinol, retinyl acetate and retinyl palmitate; vitamin B2 such as riboflavin, riboflavin butyrate and flavin adenine nucleotide, vitamin B6 such as pyridoxine hydrochloride, pyridoxine dioctanoate and pyridoxine tripalmitate, vitamin B12 and its derivatives, and vitamin B15 and its derivatives; vitamin C, such as L-ascorbic acid, L-ascorbate dipalmitate, sodium (L-ascorbic acid)-2-sulfate and dipotassium L-ascorbic acid diphosphate; vitamin D, such as ergocalciferol and cholecarciferol; vitamin E, such as $\alpha$-tocopherol, $\beta$-tocopherol, $\gamma$-tocopherol, dl-$\alpha$-tocopheryl acetate, dl-$\alpha$-tocopheryl nicotinate and dl-$\alpha$-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetyl-pantothenyl ethyl ether; biotin, and the like;

(7) Amino acids include glycine, valine, leucine, isoleucine, serine, threonine, phenylaranine, alginine, lysine, aspartic acid, glutamic acid, cystine, cysteine, methionine, and tryptophan; examples or the nucleic acids include deoxyribonucleic acid; and examples of the hormones include estradiol and ethenyl estradiol, and the like;

(8) Anti-acne agents, such as salicylic acid and its derivatives, sulfur, lactic acid, glycolic, pyruvic acid, azelaic acid, benzoyl peroxide, urea, tea tree oil, resorcinol and N-acetylcysteine, and retinoids, such as retinoic acid, and its derivatives, and the like;

(9) Antiseptics or antibacterial agents include alkyl paraoxybenzoates, benzoic acid, sodium benzoate, sorbic acid, potassium sorbate, and phenoxyethanol may be used. For the antibacterial agents, benzoic acid, benzyl peroxide, salicylic acid and its derivatives, carbolic acid, sorbic acid, paraoxybenzoic acid alkyl esters, parachloromethacresol, hexachlorophene, benzalkonium chloride, chlorohexydine chloride, trichlorocarbanilide, triclosan, photosensitizer, phenoxyethanol, and the like;

(10) Zinc salts as anti-viral and anti-bacterial agents, and also for reducing or preventing skin irritation. Examples of Zinc salts include zinc acetate, zinc lactate, zinc propionate, zinc gluconate and zinc oxide as those described in U.S. Pat. No. 5,208,031, the disclosure of which is hereby incorporated by reference. The zinc salts is at a concentration of between 0.5-25%.

(11) Tooth whitening agents include, but not limited to, hydrogen peroxide, carbimide peroxide, calcium peroxide, percarbonate, sodium percarbonate, perborates, persulfates, and mixtures thereof. Oxalic acid, malonic acid, tartaric acid and salts thereof. Suitable dicarboxylic acid salts include, but are not limited to, sodium, potassium, zinc, iron, calcium, magnesium, and copper salts of, e.g., oxalic acid, malonic acid and tartaric acid,

(12) Depilatory agents include, but are not limited to, thiol-based depilatory agents such as one or more thiol acids, (e.g. thioglycolic, thiolactic acid, and β-mercaptopropionic acid), or the alkali and/or the alkaline-earth metal salts of these acids. In addition, other active thiol agents can be used. These include β-mercaptoethanol, thioglycerols, 1,3-dithio-2-propanol, 1,4-dithio-2-butanol, 1,4-dimercapto-2,3-butanediol, 1,3-diexthio-2-methoxypropane, 1,3-dimercapto-2-aminopropane, 1,4-dimercapto-2,3-diaminobutane, aminoethanethiol, and related effective thiol actives, and the like.

(13) Fragrance oils include fragrance oils from synthetic, natural, and mixtures thereof. The perfume hydrogel compositions may be applied either as a rub in hydrogel or a spray for a sustained release of fragrance scents with or without alcohol.

(14) Insect repellants include ethyl butylacetylaminopropionate, N, N-diethyl toluamide (DEET), N, N-diethyl benzamide, dimethyl phytate, ethyl bexanediol, indalone, bicycloheptene dicarboxide, tetrahydro furaldehyde, and the like.

(15) Antioxidants include tocopherol, butylhydroxyanisole, dibutylhydroxytoluene and phytic acid;

(16) Examples of the chelating agents include alanine, sodium ethylenediaminetetraacetate, sodium polyphosphate, sodium metaphosphate and phosphoric acid;

(17) Examples of the refrigerants include L-menthol and camphor;

(18) Examples of the anti-inflammatory agents include allantoin, glycyrrhizin and salts thereof, glycyrrhetinic acid and stearyl glycyrrhetinate, tranexamic acid, azulene, and the like;

(19) Salts such as inorganic salts, salts of organic acid, amine salts and salts of amino acid. Examples of the inorganic salts include sodium, potassium, magnesium, calcium, aluminum, zirconium, and zinc salt of hydrochloric acid, sulfuric acid, carbonate acid, and nitric acid. Examples of organic acid salts include salts of acetic acid, dehydroacetic acid, citric acid, maleic acid, succinic acid, ascorbic acid, and stearic acid. An example of amine salt is salt of triethanolamine and that of amino acid salt is salt of glutamic acid. Other examples are salts of hyaluronic acid, chondroitin sulfate, aluminum zirconium glycine complex and salts made by acid-base reaction which are allowed to incorporate in cosmetics.

(20) Colorants include various dyes, organic and inorganic pigments. Example of dyes include azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors; and carbon black. Inorganic pigments include iron oxides, ultramarines, chromium, chromium hydroxide colors, and mixtures thereof. Suitable inorganic pigments include iron oxides.

Mention may also be made of colorants with an effect, such as particles comprising a natural or synthetic, organic or mineral substrate, for example glass, acrylic resins, polyester, polyurethane, polyethylene terephthalate, ceramics or aluminas, the said substrate being uncoated or coated with metallic substances, for instance aluminum, gold, silver, platinum, copper or bronze, or with metal oxides, for instance titanium dioxide, iron oxide or chromium oxide, and mixtures thereof. Interference pigments, especially liquid-crystal or multilayer interference pigments may also be used.

The water-soluble dyes are, for example, beetroot juice or methylene blue.

Other colorants may be encapsulated with water soluble materials or water insoluble materials. Products such as SUNSIL materials, encapsulated with silicone, are available from Sunjin Chemical Company. Additional dyestuffs coated with nylon or polymethyl methacrylate are also available from Sunjin Chemical Company.

(21) Particulate fillers may be colored or non-colored (non-colored meaning without color or white in color), preferably, the particulate fillers have particle size of 0.02 to 100, preferably 0.5 to 50 microns. Suitable particulate fillers include bismuth oxychloride, titanated mica, fumed silica, spherical silica, silicone powder, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, titanium dioxide, zinc laurate, zinc myristate, zinc rosinate, alumina, attapulgite, calcium carbonate, calcium silicate, dextran, kaolin, nylon, silica silylate, sericite, soy flour, tin oxide, titanium hydroxide, trimagnesium phosphate, walnut shell powder, or mixtures thereof.

(22) The above mentioned pigments and particulate fillers may be surface treated with lecithin, amino acids, mineral oil, silicone oil or various other agents either alone or in combination, which coat the particulate surface. The coating used for the surface treatment may be either lipophilic or hydrophilic in character.

As those skilled in the art will appreciate, the foregoing listing of cosmetic active ingredients is exemplary only. Because the cosmetic hydrogel compositions of the present invention are uniquely suited for utilization in a wide variety of cosmetic and personal care products and application for beauty and personal care.

In some embodiments, the hydrogel compositions of present invention comprise pharmaceutical and/or physiologically acceptable humectants which are preferably present at a level of from about 0.01% to about 40%, preferably from about 0.1% to about 30% and preferably from about 0.5% to about 25%. Preferred humectants include, but are not limited to, compounds selected from polyhydric alcohols, sorbitol, glycerol, urea, betaine, D-panthenol, DL-panthenol, calcium pantothenate, royal jelly, panthetine, pantotheine, panthenyl ethyl ether, pangamic acid, pyridoxin, pantoyl lactose Vitamin B complex, sodium pyrrolidone carboxylic acid, hexane-1,2,6, -triol, guanidine or its derivatives, and mixtures thereof.

Suitable polyhydric alcohols for use herein include, but are not limited to polyalkylene glycols and preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, pentylene glycol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. Preferred polyhydric alcohols of the present invention are selected from glycerine, butylene glycol, propylene glycol, pentylene glycol, hexylene glycol, dipropylene glycol, polyethylene glycol, hexane triol, ethoxylated glycerine and propoxylated glycerine and mixtures thereof.

Suitable humectants useful herein also include sodium 2-pyrrolidone-5-carboxylate (NaPCA), guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; betaine, panthenol and derivatives thereof; and mixtures thereof.

In some embodiments, the hydrogel compositions of present invention comprise pharmaceutical and/or physiologically acceptable emollients which are preferably present at a level of from about 0.01% to about 20%, preferably from about 0.1% to about 15% and preferably from about 0.5% to about 10%. Examples of emollients are lanolin, castor oil, mineral oil, silicone derivatives and petroleum jelly. Other compositions used as emollients include high oleic sunflower oil and its derivatives, macadamia nut oil and its derivatives, grape seed oil, hazelnut oil, olive oil, sesame oil, and other natural seed and nut oils such as jojoba oil, and derivatives thereof. Finally, other compositions used as emollients include corn oil, cottonseed oil, rose water ointment, apricot kernel oil, avocado oil, theobroma oil, almond oil, and myristyl alcohol. Additionally, a number of fatty acids derived from either plants or animal sources have been used as emollients. Fatty acids used in cosmetic formulations include stearic acid, oleic acid, myristic acid and palmitic acid. Other typical fatty acids include linoleic acid, behenic acid, and palmitoleic acid. Fatty alcohols are also used as emollients. Examples of fatty alcohols used as emollients are lauryl alcohol, cetyl alcohol, stearyl alcohol, jojoba alcohol and oleyl alcohol. Further, fatty esters are used as emollients. Examples of fatty esters include isopropyl palmitate, isopropyl myristate and glyceryl stearate. Another fatty ester emollient is ojoba oil. Further, non-biodegradable emollients, such as hydrocarbons or silicones (such as methyl silicones) are known and are used as emollients in cosmetic and personal care preparations.

In some embodiments, the hydrogel compositions of present invention further comprise surfactants which are preferably present at a level of from about 0.01% to about 15%, preferably from about 0.1% to about 10%. The surfactant may be an anionic surfactant, a cationic surfactant, an ampholytic surfactant, or a nonionic surfactant. Examples of nonionic surfactants include fatty acid esters of polyols, for-instance sorbitol or glyceryl mono-, di-, tri- or sesquioleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl) ethers. Examples of anionic surfactants include carboxylates (sodium 2-(2-hydroxyalkyloxy) acetate)), amino acid derivatives (N-acyl-glutamates, N-acylglycinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof. Examples of amphoteric and zwitterionic include betaines, N-alkylamidobetaines and derivatives thereof, glycine derivatives, sultaines, alkyl polyaminocarboxylates and alkylamphoacetates, and mixtures thereof.

In some embodiments, the hydrogel compositions of present invention further comprise rheology modifiers which are preferably present at a level of from about 0.01% to about 6%. Examples of rheology modifiers include, but not limited to, carbomers, acrylic copolymers, polyacrylamides, polysaccharides, natural gums, clays such as Laponite® from Southern Clay Products, Inc. (Gonzales, Tex.), and the like.

In some embodiments, the hydrogel compositions of the present invention comprise one or more components that facilitate penetration through the upper stratum corneum barrier to the lower levels of the skin. Examples of skin penetration enhancers include, but are not limited to, propylene glycol, azone, ethoxydiglycol, dimethyl isosorbide, urea, ethanol, dimethyl sulfoxide, and the like.

In some embodiments, the hydrogel compositions of the present invention comprise water-soluble film-forming polymers include, but are not limited to, amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/crotonic acid copolymer, acidic acrylic polymers such as (meth) acrylic acid/alkyl (meth) acrylate copolymer, (meth) acrylic acid/alkyl (meth)acrylate/alkyl acrylic amide copolymer, and amphoteric acrylic polymer such as N-methacryloyl-ethyl-N,N-dimethylammonium alpha-N-methylcarboxy-betaine/alkylmetahcrylate copolymer, hydroxypropyl (metha)acrylate/butylaminoethyl methacrylate/octyl amide of acrylic acid copolymer. Suitable water-soluble polymers are also preferably chosen from: proteins, for instance proteins of plant origin, such as wheat proteins and soya proteins; proteins of animal origin, such as keratin, for example keratin hydrolysates and sulphonic keratins; anionic, cationic, amphoteric or nonionic chitin or chitosan polymers; cellulosic polymers, such as hydroxyethylcellulose, hydroxypropylcellulose, methylcellulose, ethylhydroxyethylcellulose and carboxymethylcellulose, and quaternized cellulose derivatives; polymers of natural origin, which are optionally modified, such as: gum arabic, guar gum, xanthan derivatives, karaya gum; alginates and carrageenans; glycosaminoglycans, hyaluronic acid and derivatives thereof; shellac, sandarac gum, dammar resins, elemi gums and copal resins; deoxyribonucleic acid; mucopolysaccharides such as hyaluronic acid and chondroitin sulphate, and mixtures thereof.

In some embodiments, the hydrogel compositions of the present invention comprise preservatives. Example of physiologically tolerable preservatives include, but are not limited to, bacteriostats, preservatives, inhibitors, and the like, such as methyl, ethyl, propyl, and butyl esters of parahydroxybenzoic acid (paraben); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide; hexachlorophene; sodium benzoate; chelating agents such as ethylene diaminetetraacetic acid (EDTA), citric acid, and their alkali metal salts; phenolic compounds such as butyl hydroxyanisol, butyl hydroxytoluene, chloro- and bromo-cresols, and chloro- and bromo-oxylenols; quaternary ammonium compounds such as benzalkonium chloride; aromatic alcohols such as 2-phenylethyl alcohol and benzyl alcohol; chlorobutanol; quinoline derivatives such as iodochlorohydroxyquinoline; and the like.

In some embodiments, the hydrogel compositions of the present invention comprise pH regulators such as lactic acid, citric acid, glycolic acid, succinic acid, tartaric acid, dl-malic acid, potassium carbonate, sodium hydrogen carbonate and ammonium hydrogen carbonate; Acids or bases may also be used to adjust the pH of these formulations as needed. Various pH regulators and means for adjusting pH may be used so long as the resulting preparation is pharmaceutically and cosmetically acceptable. The hydrogel compositions preferably have a pH value in the range of about 1 to about 12. Other preferred embodiments may have a pH value in the range of about 3.5 to about 10.

In some embodiments, the hydrogel compositions of present invention comprise hair coloring agents include, but are not limited to, oxidative dyes, photographic dyes, acid dyes, neutral dyes, reactive dyes, cationic dyes, VAT dyes, and mixtures thereof, as those described in U.S. Pub. NO.: 2004/0158941, the disclosure of which is hereby incorporated by reference. A preferred hair coloring agent herein is an oxidative hair coloring agent. The total combined level of oxidative hair coloring agents in the hydrogel compositions according to the present invention is from about 0.001% to about 5%, preferably from about 0.01% to about 4%, more preferably from about 0.1% to about 3%, most preferably from about 0.1% to about 1% by weight.

The hair coloring hydrogel compositions of present invention preferably also comprise at least one oxidizing agent, which may be an inorganic or organic oxidizing agent as those described in U.S. Pub. NO.: 2004/0158941, the disclosure of which is hereby incorporated by reference. The oxidizing agent is preferably present at a level of from about 0.01% to about 10%, preferably from about 0.1% to about 6%, more preferably from about 1% to about 4% by weight of composition.

Various embodiments of present invention may also comprise additional additives, including but not limited to, silicone components such as silicone oils (such as dimethicone or cyclomethicone), water-soluble dimethicone copylyols, silicone elastomer, and emulsifier silicone elastomer, and the like. Examples of suitable silicone elastomers include those sold under the names KSG from Shin-Etsu, Trefil E-505C, Trefil E-506C, DC 9506 or DC 9701 from Dow-Corning, and those described in U.S. Pat. No. 5,266,321, the disclosure of which is incorporated by reference herein. Emulsifying elastomers such as those sold under the names of KSG-210, KSG-30, KSG-31, KSG-32, KSG-33, KSG-40, KSG-41, KSG-42, KSG-43, KSG-44 and KSG-710 from Shin-Etsu, or coated elastomers such as products sold under the denomination KSP (for example, KSP-100, KSP-200, KSP-300) sold by Shin Etsu and/or those described in U.S. Pat. No. 5,538,793, the disclosure of which is hereby incorporated by reference. A mixture of these commercial products may also be used. If present, the elastomeric compounds are preferably present in an amount of 0.01% to 15%, preferably from 0.1% to 10%.

In still other embodiments of the present invention, the hydrogel compositions may be formulated and applied as a soft or hard gel, liquid, spray, aerosols, roll-on formulation, pad-applied formulation, film-forming formulation and masks.

The present invention is further related to a method for preparing cosmetic hydrogel compositions, comprising the steps of:
(a) Dissolving the said water soluble block copolymer comprising at least two blocks of polyethylene oxide and at least one block of polypropylene oxide in water at the temperature below 20° C.,
(b) Then mixing the dissolved copolymer with other excipients and/or at least one effective amount of cosmetic active ingredients at a suitable temperature to substantially dissolve or disperse uniformly the pharmaceutical medicament or diagnostic compound in the aqueous solution, and
(c) Finally mixing the dissolved copolymer with at least one associative gelling adjuvant at a suitable temperature to form a reversely thermo-reversible cosmetic hydrogel composition.

Needless to say, a person skilled in the art will take care to select this or these optional additional compound(s), and/or the amount thereof, such that the advantageous properties of the corresponding hydrogel composition according to the present invention are not, or are not substantially, adversely affected by the envisaged addition.

In still other embodiments of present invention, there is also relates to a method and kits for preparing and delivering reversely thermo-reversible pharmaceutical and cosmetic hydrogel compositions for topical and/or mucosal applications comprising the steps of preparing and providing a pharmaceutical and cosmetic hydrogel composition in the hydrogel vehicle; and applying the hydrogel composition to the mucous membranes. The hydrogel composition is applied to the topical and/or mucosal target, in an amount sufficient to deliver a non-toxic, pharmacologically effective amount of the pharmaceutical medicament and/or cosmetic active ingredient to the intended site of treatment and/or care/beauty for a controlled or sustained release of a variety of pharmaceutical medicaments and/or cosmetic active ingredients.

A discussion of particular cosmetic and personal care applications and formulations follows.

Exemplary cosmetic and personal care applications, for which the reversely thermo-reversible hydrogel composition may be used include, but are not limited to, baby products, such as baby shampoos, lotions, and creams; bath preparations, such as bath oils, tablet and salts, bubble baths, bath fragrances and bath capsules; eye makeup preparations, such as eyebrow pencil, eyeliner, eye shadow, eye lotion, eye makeup remover and mascara; fragrance preparations, such as colognes and toilet waters, powders and sachets; noncoloring hair preparations, such as hair conditioner, hair spray, hair straighteners, permanent waves, rinses shampoos, tonics, dressings and other grooming aids; color cosmetics; hair coloring preparations such as hair dye, hair tints, hair shampoos, hair color sprays, hair lighteners and hair bleaches; makeup preparations such as foundations, leg and body paints, lipstick, makeup bases, rouges and makeup fixatives; oral hygiene products such as dentifrices and mouthwashes; personal cleanliness, such as bath soaps and detergents, deodorants, douches and feminine hygiene product; shaving preparations such as aftershave lotion, beard softeners, shaving soap and pre-shave lotions; skin care preparations such as cleansing preparations, skin antiseptics, depilatories, face and neck cleansers, body and hand cleansers, moisturizers, skin fresheners; and suntan preparations such as suntan creams, gels and lotions, indoor tanning preparations.

Preparation of the above-named cosmetic compositions and others may be accomplished with reference to any of the cosmetic formulation guidebooks and industry journals which are available in the cosmetic industry. These references supply standard formulations which may be modified by the addition or substitution of the reversible viscosifying composition of the present invention into the formulation. Suitable guidebooks include Cosmetics and Toiletries Magazine, Vol. 111 (March, 1996); Formulary: Ideas for Personal Care; Croda, Inc, Parsippany, N.J. (1993); and Cosmeticon: Cosmetic Formulary, BASF, which are hereby incorporated in their entirety by reference. The cosmetic composition may be in any form. Suitable forms include but are not limited to liquid, gel, lotions, creams, hard gel sticks, roll-ons formulations, mousses, aerosol sprays, pad-applied formulations, and film-forming formulations.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention.

The following non-limiting examples are offered as being illustrative of the properties of exemplary compositions of the present invention. In the following example, concentrations are expressed in weight percent (wt. %), and deionized water is utilized to make the formulations. Unless otherwise specified, the formulation temperature is at room temperature at about 22° C.

EXAMPLE 1

The following hydrogel vehicles comprising a water soluble block copolymer and an associative gelling adjuvant at various concentrations are prepared:

| Water soluble block copolymer Pluronic ® F 127 (wt. %) | Associative gelling adjuvant | | |
|---|---|---|---|
| | Laureth-4 (wt. %) | Sol-Gel[1] (° C.) | Gel-Sol[2] (° C.) |
| 20.0 | 0.0 | 25 | >50 |
| 19.6 | 2.0 | 18 | >50 |
| 19.1 | 4.6 | 12 | >50 |
| 18.5 | 7.9 | 7 | >50 |
| 15.2 | 0.0 | No gel formation | No gel formation |
| 15.1 | 0.5 | 34 | 43 |
| 14.9 | 1.5 | 26 | >50 |
| 14.7 | 3.4 | 21 | >50 |
| | Cromollient SCE[3] (wt. %) | Sol-Gel (° C.) | Gel-Sol (° C.) |
| 14.7 | 2.8 | 31 | N/A[4] |
| 14.4 | 5.6 | 25 | N/A |
| | Salicylic Acid (wt. %) | Sol-Gel[1] (° C.) | Gel-Sol[2] (° C.) |
| 17.3 | 3.9 | 12 | N/A[4] |
| 34.5 | 3.2 | 24 | N/A[4] |

[1]Solution to gel transition.
[2]Gel to solution transition.
[3]Di-PPG-2 Myreth-10 Adipate from Croda Inc., Edison, New Jersey.
[4]No measurement was taken.

Procedure: Pluronic® F 127 is first dissolved in water while stirring at a temperature below 10° C. After forming uniform solution, an associative gelling adjuvant is added to the polymer solution with stirring at a temperature about 4° C. All of the hydrogel compositions formed are clear and transparent.

EXAMPLE 2

The following ACNE treatment hydrogel compositions are prepared:

| | | Wt. % | |
|---|---|---|---|
| Phase | Ingredients | Formula I | Formula II |
| A | De-ionized water | 76.3 | 75.7 |
| | Propylene glycol | 3.0 | 3.9 |
| | Di-propylene glycol | 4.0 | 3.0 |
| | Sodium chloride | 0.9 | 0.9 |
| B | Pluronic ® F 127 (from BASF) | 12.0 | 11.9 |
| C | Salicylic acid | 2.1 | 2.0 |
| D | Brij L4 (from Croda | 1.7 | 2.6 |

Procedure: Combining ingredients A, and then add B with stirring at temperature below 10° C. After forming homogenous solution, add C, and continue to mix at room temperature until C dissolves. Add D to the solution dropwise and mix. It forms clear and transparent gel at room temperature. The formula I is found to be in a gel form in the temperature range from at about 9° C. to about 30° C., and formula II is found to be in a gel form in the temperature range from at about 0° C. to about 38° C.

EXAMPLE 3

The following hydrocortisone hydrogel composition is prepared:

| Phase | Ingredients | Wt. % |
|---|---|---|
| A | De-ionized water | 75.1 |
|   | Hexylene glycol | 2.0 |
|   | Di-propylene glycol | 3.0 |
| B | Pluronic ® F 127 (from BASF) | 14.0 |
| C | Hydrocortisone | 1.0 |
| D | Preservatives | 0.2 |
|   | Sodium chloride | 0.6 |
| E | Cromollient SCE (from Croda) | 1.0 |
|   | Brij L4 (from Croda) | 3.0 |

Procedure: Combining ingredients A in a beaker, add B, and mixing at a temperature below 10° C. After forming homogenous solution, adding C, and mix at room temperature until it dissolves. Add D, mix to uniform. Finally, add E dropwise and mix to uniform.

EXAMPLE 4

The following benzydamine hydrochloride hydrogel composition is prepared:

| Phase | Ingredients | Wt. % |
|---|---|---|
| A | De-ionized water | 74.7 |
|   | Glycerin | 3.0 |
|   | Di-propylene glycol | 3.0 |
| B | Pluronic ® F 127 (from BASF) | 12.5 |
| C | Benzydamine hydrochloride | 3.0 |
| D | Preservatives | 0.2 |
|   | Sodium chloride | 0.6 |
| E | Brij 14 (from Croda) | 3.0 |

Procedure: Combining ingredients A in a beaker, add B, and mixing at a temperature below 10° C. After forming homogenous solution, adding C, and mix at room temperature until it dissolves. Add D, mix to uniform. Finally, add E dropwise and mix to uniform.

EXAMPLE 5

The following anti-aging skincare hydrogel composition is prepared:

| Phase | Ingredients | Wt. % |
|---|---|---|
| A | De-ionized water | 74.4 |
|   | Glycerin | 7.0 |
|   | Di-propylene glycol | 3.0 |
| B | Pluronic ® F 127 (from BASF) | 12.0 |
| C | Salicylic acid | 0.5 |
| D | Sodium PCA | 0.1 |
|   | Collagen | 0.1 |
|   | Methylparaben | 0.2 |
| E | Brij LT3 (from Croda) | 2.6 |
| F | Fragrance | 0.1 |

Procedure: Combining ingredients A in a beaker, add B, and mixing at a temperature below 10° C. After forming homogenous solution, adding C, and mix at room temperature until it dissolves. Add D, mix to uniform solution, and then add E dropwise and mix. Finally, add F, and mix to uniform.

EXAMPLE 6

The following foundation hydrogel composition is prepared:

| Phase | Ingredients | Wt. % |
|---|---|---|
| A | De-ionized water | 70.0 |
|   | Butylene glycol | 2.0 |
|   | Di-propylene glycol | 3.0 |
| B | Pluronic ® F 127 (from BASF) | 8.0 |
| C | Laponite ® XLG (from Southern Clay Products, Inc.) | 2.0 |
| D | Pigments | 7.5 |
| E | Mica | 1.0 |
| F | KSP-100 (from Shin-Etsu) | 0.5 |
|   | Dimethicone 200 Fluid (from Dow Corning) | 0.5 |
| G | Sodium PCA | 0.1 |
|   | Vitamin E | 0.1 |
|   | Preservatives | 0.3 |
| H | Cromollient SCE (from Croda) | 5.0 |

Procedure: Combining ingredients of A, and then add B with stirring at a temperature below 10° C. After forming homogenous solution, add C, and mix at room temperature to uniform. Add D, and homogenize for 20 minutes. Add E, and mix to uniform. Add combining ingredients F and mix to uniform. Add G, and mixing to uniform. Finally, add H dropwise under stirring, and mix to uniform at room temperature.

EXAMPLE 7

The following alcohol-free insect repellant spray hydrogel composition is prepared:

| Phase | Ingredients | Wt. % |
|---|---|---|
| A | De-ionized water | 63.1 |
|   | Hexylene glycol | 4.0 |
|   | Butylene glycol | 3.0 |
| B | Pluronic ® F 127 (from BASF) | 12.5 |
| C | BAAPE (Ethyl butylacetylaminopropionate) | 12.0 |
| D | Preservatives | 0.2 |
| E | Cromollient SCE (from Creda) | 4.0 |
|   | Brij LT4 (from Croda) | 1.0 |
| F | Fragrance | 0.2 |

Procedure: Combining ingredients of A, and then add B with stirring at a temperature below 10° C. After forming homogenous solution, add C, and mix at room temperature to uniform. Add D, and mix to uniform. Add E dropwise under stirring, and mix to uniform at room temperature. Finally, add F, and mix to uniform.

EXAMPLE 8

The following sunscreen spray composition is prepared:

| Phase | Ingredients | Wt. % |
|---|---|---|
| A | De-ionized water | 40.1 |
|   | Alcohol SD 40B anhydrous | 30.0 |
|   | Hexylene glycol | 4.0 |
| B | Pluronic ® F 127 (from BASF) | 13.0 |
| C | Octyl methoxycinnamate | 5.0 |
|   | Oxybenzone | 2.5 |
| D | Aloe | 0.1 |
|   | Vitamin E | 0.2 |
| E | Cromollient SCE (from Croda) | 1.0 |
|   | Brie LT3 (from Croda) | 2.0 |
| F | Fragrance | 0.1 |

Procedure: Combining ingredients of A, and then add B with stirring at a temperature below 10° C. After forming homogenous solution, add C, and mix at room temperature to uniform. Add D, and mix to uniform. Add E dropwise under stirring, and mix to uniform at room temperature. Finally, add F, and mix to uniform. Estimated SPF 15 to 25.

EXAMPLE 9

The following topical hydrogel composition comprising terbinafine hydrochloride is prepared:

| Phase | Ingredients | wt. % |
|---|---|---|
| A | Pluronic ® F 127 | 12.0 |
|   | De-ionized water | 75.3 |
|   | PEG-400 | 3.3 |
|   | Di-propylene glycol | 2.9 |
| B | Salicylic acid | 2.0 |
| C | Terbinafine hydrochloride | 1.0 |
| D | Menthol | 0.5 |
| E | Laureth-4 | 3.0 |

Procedure: Combining ingredients A, and stirring at temperature below 10° C. to form a homogenous solution; then raised the temperature to 55-60° C., add B, and stirring until B completely dissolved; Add C at 55-60° C., and continue to stir until it is dissolved; Add D at 55-60° C., and stir until it is dissolved, Finally, add E at 55-60° C., stirring until homogenous; cool down to room temperature. The resulting preparation is a transparent gel at room temperature.

EXAMPLE 10

The following hydrogel composition comprising terbinafine hydrochloride is prepared:

| Phase | Ingredients | wt. (%) |
|---|---|---|
| A | Pluronic ® F 127 | 12.5 |
|   | De-ionized water | 75.9 |
|   | PEG-400 | 3.2 |
|   | Di-propylene glycol | 3.0 |
| B | Methyl paraben | 0.3 |
|   | Propyl paraben | 0.2 |
| C | Terbinafine hydrochloride | 1.0 |
| D | Menthol | 0.5 |
| E | Laureth-4 | 3.4 |

Procedure: Combining ingredients A, and stirring at temperature below 10° C. to form a homogenous solution; then raised the temperature to 55-60° C., add B, and stirring until B completely dissolved; Add C at 55-60° C., and continue to stir until it is dissolved; Add D at 55-60° C., and stir until it is dissolved; Finally, add E at 55-60° C., stirring until homogenous; cool down to room temperature. The resulting preparation is a liquid at room temperature and turns to a transparent gel at temperature above 24-25° C.

EXAMPLE 11

The following hydrogel composition comprising terbinafine hydrochloride is prepared:

| Phase | Ingredients | wt. % |
|---|---|---|
| A | Pluronic ® F 127 | 12.0 |
|   | De-ionized water | 80.6 |
| B | Salicylic acid | 2.0 |
| C | Terbinafine hydrochloride | 2.0 |
| D | Laureth-4 | 3.4 |

Procedure: Combining ingredients A, and stirring at temperature below 10° C. to form a homogenous solution; then raised the temperature to 55-60° C., add B, and stirring until B completely dissolved. Add C at 55-60° C., and continue to stir until it is dissolved. Finally, add D at 55-60° C., stirring until homogenous; cool down to room temperature. The resulting preparation is a transparent gel at room temperature.

EXAMPLE 12

The following topical anti-alopecia reversely thermo-reversible hydrogel composition is prepared:

| Phase | Ingredients | wt. % |
|---|---|---|
| A | De-ionized water | 76.5 |
|   | PEG-400 | 1.2 |
|   | Di-propylene glycol | 3.0 |
|   | Pluronic ® F 127 | 12.0 |
| B | Salicylic acid | 2.0 |
| C | Menthol | 0.3 |
| D | Laureth-4 | 3.0 |

Procedure: Combining ingredients A, and stirring at temperature below 10° C. to form a homogenous solution; then raised the temperature to 55-60° C., add B, and stirring until B completely dissolved; Add C at 55-60° C., and continue to stir until it is dissolved. Finally, add D at 55-60° C., stirring until homogenous; cool down to room temperature. The resulting preparation is a transparent gel at room temperature.

The topical hydrogel composition is applied to the affected area of scalp either as a leave-on or a rinse-off product.

Pilot studies were performed using the formula of Example 1 as a rinse-off treatment product. 6 healthy male volunteers with 10-20 years of hair loss history, aged 40-56 with vertex baldness and most recession of front hairline were used. Each subjects applied 1-4 ml hydrogel composition of the formula of Example 1 to the affected area of scalp, massaging it on the scalp for about 1-2 minutes, and then wash off in the shower daily. The duration of the treatment was 12 weeks. Pictures were taken before and after treatment at one week interval. The primary efficacy of treatment was evaluated manually by hair counts of the template area of the subject's scalp. It was surprisingly found that after one week application, there was appearance of new hair in the otherwise bald frontal and vertex areas in the scalp of the two subjects. After two to three weeks of application, there was appearance of new hair for rest of the four subjects. After 12 weeks of studies, four subjects had shown significant regrowth of new hair, and two subjects had shown moderate regrowth of new hair.

EXAMPLE 13

The following topical rinse-off anti-alopecia reversely thermo-reversible hydrogel composition is prepared:

| Phase | Ingredients | wt. % |
|---|---|---|
| A | De-ionized water | 75.3 |
|   | PEG-400 | 4.2 |
|   | Di-propylene glycol | 3.0 |
|   | Pluronic ® F 127 | 11.5 |
| B | Salicylic acid | 2.5 |
| C | Menthol | 0.5 |

-continued

| Phase | Ingredients | wt. % |
|---|---|---|
| D | Laureth-4 | 2.0 |
|   | Sepigel 305 | 1.0 |

Procedure: Combining ingredients A, and stirring at temperature below 10° C. to form a homogenous solution; then raised the temperature to 55-60° C., add B, and stirring until B completely dissolved. Add C at 55-60° C., and continue to stir until it is dissolved. Finally, add D at 55-60° C., stirring until homogenous; cool down to room temperature.

The composition is applied to the affected area of scalp as a rinse-off product.

EXAMPLE 14

The following topical anti-alopecia reversely thermo-reversible hydrogel composition is prepared:

| Phase | Ingredients | wt. % |
|---|---|---|
| A | De-ionized water | 75.2 |
|   | PEG-400 | 3.2 |
|   | Di-propylene glycol | 3.0 |
|   | Pluronic ® F 127 | 13.5 |
| B | Minodixil | 1.5 |
| C | Menthol | 0.2 |
| D | Laureth-4 | 3.4 |

Procedure: Combining ingredients A, and stirring at temperature below 10° C. to form a homogenous solution; then raised the temperature to 55-60° C., add B, and stirring until B completely dissolved. Add C at 55-60° C., and continue to stir until it is dissolved. Finally, add D at 55-60° C., stirring until homogenous; cool down to room temperature.

The composition is applied to the affected area of scalp as a leave-on product.

What is claimed is:

1. A reversely thermo-reversible hydrogel composition comprising:
   (a) a water soluble block copolymer having the general formula of HO-$(EO)_a(PO)_b(EO)_a$—H, where $(EO)_a$ is a polyethylene oxide block, $(PO)_b$ is a polypropylene oxide block, a is in the range of about 50 to about 150, and b is in the range of about 35 to about 70;
   (b) at least one associative gelling adjuvant having a water solubility of less than 0.5 g/100 ml being capable of forming water soluble inter-molecular complexes with said water soluble block copolymers in water; and
   (c) water,
   wherein the combined amount of the water soluble block copolymer (a) and the at least one associative gelling adjuvant (b) is 24 wt.% or less of the hydrogel composition, and
   wherein the hydrogel composition is clear and transparent and has an adjustable sol-gel transition temperature in the range of from about 4-45° C.

2. The composition of claim 1, wherein the water soluble block copolymer is present at a concentration ranging from about 5% to about 20% by weight of the total composition.

3. The composition of claim 2, wherein the water soluble block copolymer is present at a concentration ranging from about 8% to about 16% by weight of the total composition.

4. The composition of claim 1, wherein the at least one associative gelling adjuvant is present at a concentration ranging from about 0.1% to about 12% by weight of the total composition.

5. The composition of claim 1, wherein the at least one associative gelling adjuvant is selected from the group consisting of oxyalkylated fatty alcohol, esters of oxyalkylated fatty alcohol, oxyalkylated alkyl alcohol, esters of oxyalkylated alkyl alcohol, oxyalkylated alkylaryl alcohol, oxyalkylated sorbitan ester, oxyalkylated triglyceride, oxyalkylated glyceryl ester, esters of oxyalkylated sorbitol, and mixtures thereof.

6. The composition of claim 1, wherein the water soluble block copolymer comprises Poloxamer 407.

7. The composition of claim 1, wherein the at least one gelling adjuvant comprises Di-PPG-2 Myreth-10 Adipate.

8. The composition of claim 1, further comprising an effective amount of at least one of a pharmaceutical medicament, a diagnostic compound, and a cosmetic active agent.

9. The composition of claim 8, wherein the pharmaceutical medicament, diagnostic compound, and cosmetic active agent is selected from the group consisting of anti-bacterial substances, anti-histamines, decongestants, anti-inflammatories, miotics, anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal agents, annoebacidal compounds, trichomonacidal agents, analgesics, anti-arthritics, anti-asthmatics, anti-coagulants, anti-convulsants, anti-depressants, anti-diabetics, anti-neoplastics, anti-psychotics, anti-hypertensive agents, muscle relaxants, proteins, peptides, acne treatment agents, lubricating agents, anti-alopecia agents, essential oils, moisture retention agents, skin-beautifying agents, sun screens, antiperspirants, vitamins, amino acids, antiseptics, tooth whitening agents, depilatory agents, fragrance oils, insect repellants, antioxidants, chelating agents, refrigerants, salts, colorants, particulate fillers, and mixtures thereof.

10. The composition of claim 8, wherein at least one of the pharmaceutical medicament, diagnostic compound, and cosmetic active agent is present at a concentration ranging from about 0.001% to about 70% by weight of the total composition.

11. The composition of claim 8, further comprising at least one of a pharmaceutically and/or cosmetic acceptable humectant, emollient, surfactant, rheology modifier, skin penetration enhancer, flavoring, water soluble film forming polymer, preservative, pH regulator, and fragrance.

12. A reversely thermo-reversible hydrogel composition comprising:
   (a) a poloxamer having the general formula of HO-$(EO)_a(PO)_b(EO)_a$—H, where $(EO)_a$ is a polyethylene oxide block, $(PO)_b$ is a polypropylene oxide block, a is in the range of about 50 to about 150, and b is in the range of about 35 to about 70;
   (b) at least one associative gelling adjuvant selected from the group consisting of oxyalkylated fatty alcohols, esters of oxyalkylated fatty alcohols, esters of oxyalkylated alkyl alcohols and mixtures thereof;
   (c) an effective amount of at least one of a pharmaceutical medicament, a diagnostic compound, and a cosmetic active agent; and (d) water, wherein the combined amount of the poloxamer and the at least one associative gelling adjuvant is 24 wt. % or less of the hydrogel composition, and wherein the hydrogel composition is clear and transparent and has an adjustable sol-gel transition temperature in the range of from about 20-38° C.

13. The composition of claim 12, wherein the poloxamer is Poloxamer 407.

14. The composition of claim 12, wherein the at least one associative gelling adjuvant is Di-PPG-2 Myreth-10 Adipate.

15. The composition of claim 12, wherein the at least one pharmaceutical medicament comprises estradiol.

16. The composition of claim 12, wherein the sol-gel transition temperature is in the range of 28-35° C.

17. The composition of claim 12, further comprising at least one of a pharmaceutically and/or dermatologically acceptable humectant, emollient, surfactant, rheology modifier, skin penetration enhancer, flavoring, water soluble film forming polymer, preservative, pH regulator, and fragrance.

18. A method of treating an ophthalmic disorder comprising applying a composition according to claim 1 in liquid form to an eye and allowing the composition to gel upon contact with the eye.

19. The method of claim 18, wherein the composition further comprises an effective amount of a pharmaceutical medicament.

20. The method of claim 19, wherein the pharmaceutical medicament comprises an estradiol.

\* \* \* \* \*